(12) United States Patent
Simpson et al.

(10) Patent No.: US 9,907,497 B2
(45) Date of Patent: Mar. 6, 2018

(54) ANALYTE SENSOR

(71) Applicant: DexCom, Inc., San Diego, CA (US)

(72) Inventors: Peter C. Simpson, Encinitas, CA (US);
Robert J. Boock, Carlsbad, CA (US);
Apurv Ullas Kamath, San Diego, CA
(US); Matthew D. Wightlin, San
Diego, CA (US); Michael J. Estes, San
Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 14/057,720

(22) Filed: Oct. 18, 2013

(65) Prior Publication Data

US 2014/0046148 A1 Feb. 13, 2014

Related U.S. Application Data

(63) Continuation of application No. 12/829,264, filed on Jul. 1, 2010.
(Continued)

(51) Int. Cl.
*A61B 5/05* (2006.01)
*A61B 5/1473* (2006.01)
(Continued)

(52) U.S. Cl.
CPC .......... *A61B 5/1473* (2013.01); *A61B 5/1451* (2013.01); *A61B 5/14503* (2013.01);
(Continued)

(58) Field of Classification Search
CPC ............ A61B 51/1486; A61B 5/14865; A61B 2560/0223; A61B 2562/0209;
(Continued)

(56) References Cited

U.S. PATENT DOCUMENTS 4,206,755 A 6/1980 Klein
4,225,410 A 9/1980 Pace
(Continued)

FOREIGN PATENT DOCUMENTS

EP 1 205 753 A2 5/2002
EP 1 288 308 A1 3/2003
(Continued)

OTHER PUBLICATIONS

Baker et al. 1996. Dynamic delay and maximal dynamic error in continuous biosensors. Anal Chem 68(8):1292-1297.
(Continued)

*Primary Examiner* — Navin Natnithithadha
*Assistant Examiner* — Eric Messersmith
(74) *Attorney, Agent, or Firm* — Knobbe Martens Olson & Bear, LLP

(57) ABSTRACT

Devices and methods are provided for continuous measurement of an analyte concentration. The device can include a sensor having a plurality of sensor elements, each having at least one characteristic that is different from other sensor(s) of the device. In some embodiments, the plurality of sensor elements are each tuned to measure a different range of analyte concentration, thereby providing the device with the capability of achieving a substantially consistent level of measurement accuracy across a physiologically relevant range. In other embodiments, the device includes a plurality of sensor elements each tuned to measure during different time periods after insertion or implantation, thereby providing the sensor with the capability to continuously and accurately measure analyte concentrations across a wide range of time periods. For example, a sensor system 180 is provided having a first working electrode 150 comprising a first sensor element 102 and a second working electrode 160 comprising a second sensor element 104, and a reference
(Continued)

electrode 108 for providing a reference value for measuring the working electrode potential of the sensor elements 102, 104.

16 Claims, 8 Drawing Sheets

Related U.S. Application Data

(60) Provisional application No. 61/222,716, filed on Jul. 2, 2009, provisional application No. 61/222,815, filed on Jul. 2, 2009, provisional application No. 61/222,751, filed on Jul. 2, 2009.

(51) Int. Cl.
*A61B 5/145* (2006.01)
*A61B 5/1486* (2006.01)
*B05C 3/10* (2006.01)

(52) U.S. Cl.
CPC ...... *A61B 5/14517* (2013.01); *A61B 5/14532* (2013.01); *A61B 5/14546* (2013.01); *A61B 5/14865* (2013.01); *B05C 3/10* (2013.01); *A61B 2560/0223* (2013.01); *A61B 2562/0209* (2013.01); *A61B 2562/043* (2013.01); *A61B 2562/125* (2013.01)

(58) Field of Classification Search
CPC ........ A61B 2562/125; A61B 2562/043; A61B 5/14532; A61B 5/1473; A61B 5/1451; A61B 5/14517; A61B 5/145; B05C 3/10
USPC ................. 600/318, 345, 347, 364
See application file for complete search history.

(56) References Cited

U.S. PATENT DOCUMENTS

| | | |
|---|---|---|
| 4,568,444 A | 2/1986 | Nakamura et al. |
| 4,655,880 A | 4/1987 | Liu |
| 4,703,756 A | 11/1987 | Gough et al. |
| 4,711,245 A | 12/1987 | Higgins et al. |
| 4,736,748 A | 4/1988 | Nakamura et al. |
| 4,739,380 A | 4/1988 | Lauks et al. |
| 4,837,049 A | 6/1989 | Byers et al. |
| 4,925,444 A | 5/1990 | Orkin et al. |
| 4,935,345 A | 6/1990 | Guilbeau et al. |
| 4,974,592 A | 12/1990 | Branco |
| 5,002,055 A | 3/1991 | Merki et al. |
| 5,352,351 A | 10/1994 | White et al. |
| 5,497,772 A | 3/1996 | Schulman et al. |
| 5,513,636 A | 5/1996 | Palti |
| 5,593,852 A | 1/1997 | Heller et al. |
| 5,676,651 A | 10/1997 | Larson et al. |
| 5,711,861 A | 1/1998 | Ward et al. |
| 5,904,666 A | 5/1999 | Dedecker et al. |
| 5,904,708 A | 5/1999 | Goedeke |
| 5,957,854 A | 9/1999 | Besson et al. |
| 5,959,191 A | 9/1999 | Lewis et al. |
| 5,965,380 A | 10/1999 | Heller et al. |
| 5,967,986 A | 10/1999 | Cimochowski et al. |
| 5,985,693 A | 11/1999 | Leedy |
| 5,999,848 A | 12/1999 | Gord et al. |
| 6,016,448 A | 1/2000 | Busacker et al. |
| 6,032,667 A | 3/2000 | Heinonen |
| 6,066,448 A | 5/2000 | Wohlstadter et al. |
| 6,083,710 A | 7/2000 | Heller et al. |
| 6,088,608 A | 7/2000 | Schulman et al. |
| 6,091,975 A | 7/2000 | Daddona et al. |
| 6,117,290 A | 9/2000 | Say et al. |
| 6,121,009 A | 9/2000 | Heller et al. |
| 6,122,536 A | 9/2000 | Sun et al. |
| 6,162,611 A | 12/2000 | Heller et al. |
| 6,164,921 A | 12/2000 | Moubayed et al. |
| 6,175,767 B1 | 1/2001 | Doyle et al. |
| 6,212,416 B1 | 4/2001 | Ward et al. |
| 6,223,080 B1 | 4/2001 | Thompson |
| 6,223,083 B1 | 4/2001 | Rosar |
| 6,230,059 B1 | 5/2001 | Duffin |
| 6,284,478 B1 | 9/2001 | Heller et al. |
| 6,329,161 B1 | 12/2001 | Heller et al. |
| 6,400,974 B1 | 6/2002 | Lesho |
| 6,432,050 B1 | 8/2002 | Porat et al. |
| 6,447,448 B1 | 9/2002 | Ishikawa et al. |
| 6,466,810 B1 | 10/2002 | Ward et al. |
| 6,514,718 B2 | 2/2003 | Heller et al. |
| 6,546,268 B1 | 4/2003 | Ishikawa et al. |
| 6,558,351 B1 | 5/2003 | Steil et al. |
| 6,609,071 B2 | 8/2003 | Shapiro et al. |
| 6,749,587 B2 | 6/2004 | Flaherty |
| 6,809,507 B2 | 10/2004 | Morgan et al. |
| 6,881,551 B2 | 4/2005 | Heller et al. |
| 7,033,322 B2 | 4/2006 | Silver |
| 7,081,195 B2 | 7/2006 | Simpson et al. |
| 7,169,289 B2 | 1/2007 | Schulein et al. |
| 7,226,978 B2 | 6/2007 | Tapsak et al. |
| 7,267,665 B2 | 9/2007 | Steil et al. |
| 7,354,420 B2 | 4/2008 | Steil et al. |
| 7,366,556 B2 | 4/2008 | Brister et al. |
| 7,399,277 B2 | 7/2008 | Saidara et al. |
| 7,402,153 B2 | 7/2008 | Steil et al. |
| 7,615,007 B2 | 11/2009 | Shults et al. |
| 7,640,048 B2 | 12/2009 | Dobbles et al. |
| 2002/0042090 A1 | 4/2002 | Heller et al. |
| 2002/0042561 A1 | 4/2002 | Schulman et al. |
| 2002/0128546 A1 | 9/2002 | Silver |
| 2002/0151816 A1 | 10/2002 | Rich et al. |
| 2003/0050546 A1 | 3/2003 | Desai et al. |
| 2003/0076082 A1 | 4/2003 | Morgan et al. |
| 2003/0130616 A1 | 7/2003 | Steil et al. |
| 2003/0134347 A1 | 7/2003 | Heller et al. |
| 2003/0203498 A1 | 10/2003 | Neel et al. |
| 2004/0039298 A1 | 2/2004 | Abreu |
| 2004/0152187 A1 | 8/2004 | Haight et al. |
| 2004/0176672 A1 | 9/2004 | Silver et al. |
| 2004/0180391 A1 | 9/2004 | Gratzl et al. |
| 2005/0027182 A1 | 2/2005 | Siddiqui et al. |
| 2005/0107677 A1 | 5/2005 | Ward et al. |
| 2005/0112358 A1 | 5/2005 | Potyrailo et al. |
| 2006/0003398 A1 | 1/2006 | Heller et al. |
| 2006/0079740 A1 | 4/2006 | Silver et al. |
| 2006/0142651 A1 | 6/2006 | Brister et al. |
| 2006/0155180 A1 | 7/2006 | Brister et al. |
| 2006/0183985 A1 | 8/2006 | Brister et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258929 A1* | 11/2006 | Goode et al. ............... 600/345 |
| 2007/0016381 A1 | 1/2007 | Kamath et al. |
| 2007/0038044 A1 | 2/2007 | Dobbles et al. |
| 2007/0059196 A1 | 3/2007 | Brister et al. |
| 2007/0066873 A1 | 3/2007 | Kamath et al. |
| 2007/0131549 A1 | 6/2007 | Cai et al. |
| 2007/0151868 A1* | 7/2007 | Staib et al. ............... 205/792 |
| 2007/0151869 A1 | 7/2007 | Heller et al. |
| 2007/0163880 A1 | 7/2007 | Woo et al. |
| 2007/0197889 A1 | 8/2007 | Brister et al. |
| 2007/0203407 A1 | 8/2007 | Hoss et al. |
| 2007/0215491 A1 | 9/2007 | Heller et al. |
| 2007/0218097 A1 | 9/2007 | Heller et al. |
| 2007/0225675 A1 | 9/2007 | Robinson et al. |
| 2007/0244379 A1 | 10/2007 | Boock et al. |
| 2008/0027301 A1 | 1/2008 | Ward et al. |
| 2008/0086042 A1 | 4/2008 | Brister et al. |
| 2008/0086044 A1 | 4/2008 | Brister et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0154101 A1 | 6/2008 | Jain et al. |
| 2008/0200788 A1 | 8/2008 | Brister et al. |
| 2008/0200789 A1 | 8/2008 | Brister et al. |

(56) References Cited

U.S. PATENT DOCUMENTS

| | | |
|---|---|---|
| 2008/0200791 A1 | 8/2008 | Simpson et al. |
| 2008/0287766 A1 | 11/2008 | Rasdal et al. |
| 2009/0018424 A1 | 1/2009 | Kamath et al. |
| 2009/0054748 A1* | 2/2009 | Feldman .............. A61B 5/0031 600/316 |
| 2009/0099435 A1 | 4/2009 | Say et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0156924 A1 | 6/2009 | Shariati et al. |
| 2010/0030045 A1 | 2/2010 | Gobblieb et al. |
| 2011/0024307 A1 | 2/2011 | Simpson et al. |

FOREIGN PATENT DOCUMENTS

| | | |
|---|---|---|
| EP | 1 491 882 A2 | 12/2004 |
| EP | 1 582 864 A1 | 10/2005 |
| EP | 1 987 761 A1 | 11/2008 |
| WO | WO 90/07575 | 7/1990 |
| WO | WO 94/09507 | 4/1994 |
| WO | WO 94/29705 | 12/1994 |
| WO | WO 94/29706 | 12/1994 |
| WO | WO 96/05501 | 2/1996 |
| WO | WO 96/06947 | 3/1996 |
| WO | WO 96/36296 | 11/1996 |
| WO | WO 97/01986 | 1/1997 |
| WO | WO 98/24358 | 6/1998 |
| WO | WO 98/38904 | 9/1998 |
| WO | WO 99/13574 | 3/1999 |
| WO | WO 99/27848 | 6/1999 |
| WO | WO 99/59464 | 11/1999 |
| WO | WO 00/019887 | 4/2000 |
| WO | WO 00/030530 | 6/2000 |
| WO | WO 00/032098 | 6/2000 |
| WO | WO 00/033065 | 6/2000 |
| WO | WO 00/074753 | 12/2000 |
| WO | WO 01/016579 | 3/2001 |
| WO | WO 03/022128 | 3/2003 |
| WO | WO 03/036310 | 5/2003 |
| WO | WO 03/088832 | 10/2003 |
| WO | WO 04/060455 | 7/2004 |
| WO | WO 04/110256 | 12/2004 |
| WO | WO 04/113901 | 12/2004 |
| WO | WO 05/012900 | 2/2005 |
| WO | WO 05/034746 | 4/2005 |
| WO | WO 05/065537 | 7/2005 |
| WO | WO 05/065538 | 7/2005 |
| WO | WO 05/089103 | 9/2005 |
| WO | WO 05/121785 | 12/2005 |
| WO | WO 06/017358 | 2/2006 |
| WO | WO 06/060806 | 6/2006 |
| WO | WO 06/130268 | 12/2006 |
| WO | WO 06/133171 | 12/2006 |
| WO | WO 07/079025 | 7/2007 |
| WO | WO 07/097754 | 8/2007 |
| WO | WO 07/101223 | 9/2007 |
| WO | WO 07/127622 | 11/2007 |
| WO | WO 07/127880 | 11/2007 |
| WO | WO 07/130239 | 11/2007 |
| WO | WO 08/005780 | 1/2008 |
| WO | WO 08/048709 | 4/2008 |
| WO | WO 08/051762 | 5/2008 |
| WO | WO 08/051924 | 5/2008 |
| WO | WO 08/052199 | 5/2008 |
| WO | WO 08/076868 | 6/2008 |
| WO | WO 08/082974 | 7/2008 |
| WO | WO 08/082979 | 7/2008 |
| WO | WO 08/086541 | 7/2008 |
| WO | WO 08/094249 | 8/2008 |
| WO | WO 08/134146 | 11/2008 |
| WO | WO 08/135453 | 11/2008 |
| WO | WO 08/150917 | 12/2008 |

OTHER PUBLICATIONS

Biermann et al. 2008. How would patients behave if they were continually informed of their blood glucose levels? A simulation study using a "virtual" patient. Diab. Thechnol. & Therapeut., 10:178-187.

Bisenberger et al. 1995. A triple-step potential waveform at enzyme multisensors with thick-film gold electrodes for detection of glucose and sucrose. Sensors and Actuators, B 28:181-189.

Cameron et al. 1997. Micromodular Implants to provide electrical stimulation of paralyzed muscles and limbs. IEEE Transactions on Biomedical Engineering 44(9):781-790.

Csoregi et al., 1994. Design, characterization, and one-point in vivo calibration of a subcutaneously implanted glucose electrode. Anal Chem. 66(19):3131-3138.

Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 16-18, 2004, 18 pp.

Jaremko et al. 1998. Advances toward the implantable artificial pancreas for treatment of diabetes. Diabetes Care 21(3):444-450.

Jeutter et al. 1993. Design of a radio-linked implantable cochlear prosthesis using surface acoustic wave devices. IEEE Transactions on ultrasonics, ferroelectrics and frequency control 40(5):469-477.

Kraver et al. 2001. A mixed-signal sensor interface microinstrument. Sensors and Actuators A 91:266-277.

McGrath et al. 1995. The use of differential measurements with a glucose biosensor for interference compensation during glucose determinations by flow injection analysis. Biosens Bioelectron 10:937-943.

Pichert et al. 2000. Issues for the coming age of continuous glucose monitoring Diabetes Educ 26(6):969-980.

Smith et al. 1998. An externally powered, multichannel, implantable stimulator-telemeter for control of paralyzed muscle. IEEE Transactions on Biomedical Engineering 45(4):463-475.

Ziaie et al. 1997. A single-channel implantable microstimulator for functional neuromuscular stimulation. IEEE Transactions on Biomedical Engineering 44(10):909-920.

ISR dated Feb. 10, 2011 for PCT/US2010/040838, filed Jul. 1, 2010.

IPRP and WO dated Jan. 4, 2012 for PCT/US2010/040838, filed Jul. 1, 2010.

* cited by examiner

ANALYTE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 12/829,264, filed Jul. 1, 2010, which claims the benefit of priority under 35 U.S.C. § 119(e) of U.S. Provisional Application No. 61/222,716 filed Jul. 2, 2009, U.S. Provisional Application No. 61/222,815 filed Jul. 2, 2009, and U.S. Provisional Application No. 61/222,751 filed Jul. 2, 2009, the disclosures of which are hereby expressly incorporated by reference in their entirety and are hereby expressly made a portion of this application.

FIELD OF THE INVENTION

The embodiments described herein relate generally to devices, systems, and methods for measuring an analyte in a host.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood glucose values. Many conventional implantable glucose sensors suffer from complications within the body and provide only short-term or less-than-accurate sensing of blood glucose. Additionally, many conventional transcutaneous and intravascular sensors have problems in accurately sensing and reporting back analyte values continuously over extended periods of time due to non-analyte-related signals caused by interfering species or unknown noise-causing events.

SUMMARY OF THE INVENTION

In a first aspect, a sensor system for measurement of an analyte concentration in a host is provided, the sensor system comprising: a first sensor element configured to measure an analyte concentration in a host over a first range of analyte concentrations; and a second sensor element configured to measure analyte concentration in the host over a second range of analyte concentrations, wherein the first range of analyte concentrations and the second range of analyte concentrations are different.

In an embodiment of the first aspect, the first range of analyte concentrations and the second range of analyte concentrations are both within a physiologically relevant range.

In an embodiment of the first aspect, the first range of analyte concentrations and the second range of analyte concentrations each comprise only a portion of the physiologically relevant range.

In an embodiment of the first aspect, the first range of analyte concentrations and the second range of analyte concentrations overlap partially, but not completely.

In an embodiment of the first aspect, the analyte is glucose, and wherein the first range of analyte concentrations is from about 30 mg/dL to about 120 mg/dL and the second range of analyte concentrations is from about 80 mg/dL to about 400 mg/dL.

In an embodiment of the first aspect, a lowest value of the second range of analyte concentrations is greater than a lowest value of the first range of analyte concentrations.

In an embodiment of the first aspect, the first sensor element and the second sensor element have different sensitivities.

In an embodiment of the first aspect, the sensitivity of the first sensor element is greater than the sensitivity of the second sensor element.

In an embodiment of the first aspect, the analyte is glucose, and wherein the first sensor element has a sensitivity of from about 1 pA/mg/dL to about 100 pA/mg/dL.

In an embodiment of the first aspect, the analyte is glucose, and wherein the second sensor element has a sensitivity of from about 20 pA/mg/dL to about 300 pA/mg/dL.

In an embodiment of the first aspect, the first sensor element and the second sensor element have different current densities.

In an embodiment of the first aspect, the analyte is glucose, and wherein the first sensor element has a current density of from about 3 $pA/mg/dL/mm^2$ to about 325 $pA/mg/dL/mm^2$.

In an embodiment of the first aspect, the analyte is glucose, and wherein the second sensor element has a current density of from about 65 $pA/mg/dL/mm^2$ to about 1,000 $pA/mg/dL/mm^2$.

In an embodiment of the first aspect, a lowest value of the first range of analyte concentrations is less than a lowest value of the second range of analyte concentrations.

In an embodiment of the first aspect, the first sensor element and the second sensor element have different analyte-related to non-analyte-related signal ratios.

In an embodiment of the first aspect, the analyte-related to non-analyte-related signal ratio of the first sensor element is greater than the analyte-related to non-analyte-related signal ratio of the second sensor element.

In an embodiment of the first aspect, the analyte is glucose, and wherein the sensor system is capable of achieving an accuracy of analyte concentration measurements wherein the measurements are within +/−20% of a true analyte concentration value 80% of the time during a time period greater than about 7 days.

In an embodiment of the first aspect, the first sensor element comprises a first membrane and the second sensor element comprises a second membrane, wherein the first membrane is different from the second membrane In an embodiment of the first aspect, the first membrane and the second membrane have different membrane properties.

In an embodiment of the first aspect, the first membrane comprises a resistance domain different from a resistance domain of the second membrane.

In an embodiment of the first aspect, the first membrane comprises an interference domain different from an interference domain of the second membrane.

In an embodiment of the first aspect, the first membrane and the second membrane have a different number of domains.

In an embodiment of the first aspect, the first membrane and the second membrane each comprise glucose oxidase configured to generate hydrogen peroxide by reaction of glucose and oxygen with the glucose oxidase, wherein the first sensor element comprises an electrode configured to measure at least some of the hydrogen peroxide generated within the first membrane, and wherein the second sensor element comprises an electrode configured to measure at least some of the hydrogen peroxide generated within the second membrane.

In an embodiment of the first aspect, the first membrane is configured to consume more hydrogen peroxide than the second membrane.

In an embodiment of the first aspect, the first membrane is configured to direct more hydrogen peroxide to the first electrode than the second membrane system directs to the second electrode.

In an embodiment of the first aspect, at least one membrane selected from the group consisting of the first membrane and the second membrane is configured to recycle and/or reuse the hydrogen peroxide for a purpose other than for measurement.

In an embodiment of the first aspect, wherein the sensor system further comprises sensor electronics operably connected to the first sensor element and the second sensor elements wherein the sensor electronics comprise at least one potentiostat.

In an embodiment of the first aspect, the at least one potentiostat is configured to apply a first bias potential to the first sensor element and a second bias potential to the second sensor element, wherein the first bias potential is different from the second bias potential.

In an embodiment of the first aspect, the first bias potential is less than the second bias potential.

In an embodiment of the first aspect, a highest concentration of the first range of analyte concentrations is less than the lowest concentration of the second range of analyte concentrations.

In an embodiment of the first aspect, the sensor system is configured for implantation wholly in a tissue of a host.

In an embodiment of the first aspect, the sensor system is configured for transcutaneous placement through a skin of a host.

In an embodiment of the first aspect, the sensor system is configured for non-invasive measurement through a skin of a host.

In an embodiment of the first aspect, the sensor system is configured for fluid communication with a vascular system of a host.

In an embodiment of the first aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In a second aspect, a sensor system for measurement of an analyte concentration in a host is provided, the sensor system comprising: a first sensor element configured to measure analyte concentrations over a first range at a first current density; and a second sensor element configured to measure analyte concentrations over a second range at a second current density, wherein the first current density and the second current density are different.

In an embodiment of the second aspect, the first current density is greater than the second current density.

In an embodiment of the second aspect, the highest concentration of the first range is less than the lowest concentration of the second range.

In an embodiment of the second aspect, the analyte is glucose, and wherein the first sensor element has a sensitivity of from about 1 pA/mg/dL to about 100 pA/mg/dL.

In an embodiment of the second aspect, the analyte is glucose, and wherein the second sensor element has a sensitivity of from about 20 pA/mg/dL to about 300 pA/mg/dL.

In an embodiment of the second aspect, the analyte is glucose, and wherein the first second element has a current density of from about 3 pA/mg/dL/mm$^2$ to about 325 pA/mg/dL/mm$^2$ In an embodiment of the second aspect, the analyte is glucose, and wherein the second sensor element has a current density of from about 65 pA/mg/dL/mm$^2$ to about 1,000 pA/mg/dL/mm$^2$.

In an embodiment of the second aspect, the system is configured to measure at least one of a current selected from the group consisting of a current produced by the first sensor element and a current produced by the second sensor element with substantial linearity at glucose concentrations of up to about 400 mg/dL in fluid with an oxygen concentration of less than about 0.6 mg/L.

In a third aspect, a sensor system for measurement of an analyte concentration in a host is provided, the sensor system comprising: a plurality of sensor elements, each wherein each sensor element is configured for measurement over a different range of analyte concentrations, wherein the plurality of sensor elements comprise: a first sensor element comprising a first membrane; and a second sensor element comprising a second membrane; wherein the first sensor membrane and the second sensor membrane have different membrane properties.

In an embodiment of the third aspect, the first membrane comprises a resistance domain different from a resistance domain of the second membrane.

In an embodiment of the third aspect, the first membrane comprises an interference domain different from an interference domain of the second membrane.

In an embodiment of the third aspect, a number of domains of the first membrane and a number of domains of the second membrane are different.

In an embodiment of the third aspect, the first membrane and the second membrane each comprise glucose oxidase configured to generate hydrogen peroxide by reaction of glucose and oxygen with the glucose oxidase, wherein the first sensor element comprises an electrode configured to measure at least some of the hydrogen peroxide generated within the first membrane, and wherein the second sensor element comprises an electrode configured to measure at least some of the hydrogen peroxide generated within the second membrane.

In an embodiment of the third aspect, the first membrane is configured to consume more hydrogen peroxide than the second membrane.

In an embodiment of the third aspect, the first membrane is configured to direct more hydrogen peroxide to the first electrode than the second membrane directs to the second electrode.

In an embodiment of the third aspect, at least one membrane selected from the group consisting of the first membrane and the second membrane is configured to recycle and/or reuse the hydrogen peroxide for a purpose other than for measurement.

In an embodiment of the third aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In a fourth aspect, a sensor system for measurement of an analyte concentration in a host is provided, the sensor system comprising: a plurality of sensor elements, each configured to measure analyte concentrations over different time periods of in vivo implantation, wherein the plurality of sensor elements comprises a first sensor element configured to measure analyte concentrations over a first time period of in vivo implantation and a second sensor element configured to measure analyte concentrations over a second time period of in vivo implantation.

In an embodiment of the fourth aspect, the first time period is during an initial period of in vivo implantation, wherein the second time period is during a second time period of in vivo implantation, and wherein the second period begins after the initial period has begun.

In an embodiment of the fourth aspect, the first time period and the second time period overlap partially, but not completely.

In an embodiment of the fourth aspect, the first time period is from about day 1 post-implantation to about day 3 post-implantation and the second time period is from about day 2 post-implantation to about day 10 post-implantation.

In an embodiment of the fourth aspect, the first time period is from about day 1 post-implantation to about day 21 post-implantation and the second time period is from about day 10 post-implantation to about year 1 post-implantation.

In an embodiment of the fourth aspect, the first sensor element comprises a first biointerface membrane and the second sensor element comprises a second biointerface membrane, and wherein the first biointerface membrane has at least one property different from that of the second biointerface membrane.

In an embodiment of the fourth aspect, the first biointerface membrane comprises a three dimensional architecture.

In an embodiment of the fourth aspect, the second biointerface membrane comprises a three dimensional architecture that is different from the three dimensional architecture of the first biointerface membrane.

In an embodiment of the fourth aspect, the three dimensional architecture of the first biointerface membrane comprises pores within a first range of sizes and the three dimensional architecture of the second biointerface membranes comprises pores within a second range of sizes, wherein the largest size of the first range of sizes is smaller than the smallest size of the second range of sizes.

In an embodiment of the fourth aspect, the sensor system is configured for implantation wholly in a tissue of a host.

In an embodiment of the fourth aspect, the sensor system is configured for transcutaneous placement through a skin of a host.

In an embodiment of the fourth aspect, the sensor system is configured for fluid communication with a vascular system of a host.

In an embodiment of the fourth aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In a fifth aspect, a method for processing data from a sensor system configured for measurement of an analyte concentration in a host is provided, the method comprising: calibrating a first sensor element, wherein the first sensor element is configured to measure an analyte concentration within a first range of analyte concentrations; and calibrating a second sensor element, wherein the second sensor element is configured to measure an analyte concentration within a second range of analyte concentrations, wherein the second range is different from the first range.

In an embodiment of the fifth aspect, calibrating the first sensor element comprises receiving an external reference value.

In an embodiment of the fifth aspect, calibrating the first sensor element comprises receiving a calibration value provided by a manufacturer.

In an embodiment of the fifth aspect, calibrating the first sensor element comprises performing a first algorithm.

In an embodiment of the fifth aspect, calibrating the first sensor element further comprises performing a second algorithm, and wherein the second algorithm is different from the first algorithm.

In an embodiment of the fifth aspect, the first range and second range partially, but not completely, overlap within an overlapping range.

In an embodiment of the fifth aspect, calibrating the first sensor element comprises receiving an external reference value within the overlapping range.

In an embodiment of the fifth aspect, calibrating the second sensor element comprises receiving a value obtained from the first sensor element.

In an embodiment of the fifth aspect, the first sensor element and the second sensor element each have different current densities, and wherein calibrating the second sensor element utilizes a known relationship between the current density of the first sensor element and the current density of the second sensor elements.

In an embodiment of the fifth aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In a sixth aspect, a method for processing data from a sensor system configured for measurement of an analyte concentration in a host is provided, the method comprising: processing a first signal from a first sensor element, wherein the first sensor element is configured to measure an analyte concentration in a first range, and wherein the first signal is associated with the analyte concentration; and processing a second signal from a second sensor element, wherein the second sensor element is configured to measure an analyte concentration in a second range, wherein the second signal is associated with the analyte concentration, and wherein the first range is different from the second range.

In an embodiment of the sixth aspect, at least one of processing the first signal or processing the second signal comprises comparing the first signal to the second signal.

In an embodiment of the sixth aspect, at least one of processing the first signal or processing the second signal comprises averaging and/or integrating the first signal to the second signal.

In an embodiment of the sixth aspect, at least one of processing the first signal or processing the second signal comprises polling the first signal to the second signal.

In an embodiment of the sixth aspect, at least one of processing the first signal or processing the second signal comprises evaluating an accuracy of the first signal.

In an embodiment of the sixth aspect, the method further comprises: calibrating the first signal to generate a first calibrated signal; and calibrating the second signal to generate a second calibrated signal.

In an embodiment of the sixth aspect, at least one of processing the first signal or processing the second signal comprises evaluating an accuracy of the first calibrated signal and an accuracy of the second calibrated signal.

In an embodiment of the sixth aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In a seventh aspect, a method for manufacturing a sensor system configured for measurement of an analyte concentration in a host, the method comprising: manufacturing a first sensor element configured to measure an analyte concentration in a first range; and manufacturing a second sensor element configured to measure an analyte concentration in a second range, wherein the second range is different from the first range.

In an embodiment of the seventh aspect, manufacturing the first sensor element comprises forming a first electrode, and wherein manufacturing the second sensor element comprises forming a second electrode.

In an embodiment of the seventh aspect, manufacturing the first sensor element further comprises forming a first membrane on the first electrode, and wherein manufacturing the second sensor element further comprises forming a second membrane on the second electrode.

In an embodiment of the seventh aspect, the first membrane is configured to provide a first current density and the second membrane is configured to provide a second current density, and wherein the first current density is different from the second current density.

In an embodiment of the seventh aspect, forming the first membrane and forming the second membrane comprise optically curing the first membrane and the second membrane so as to provide a different sensitivity for the first membrane and the second membrane.

In an embodiment of the seventh aspect, optically curing the first membrane and the second membrane comprise using selective photolithography so as to provide a different current density for the first membrane and the second membrane.

In an embodiment of the seventh aspect, using selective photolithography comprises masking the first membrane during at least a portion of the photolithographic exposure of the second membrane.

In an embodiment of the seventh aspect, curing the first membrane and the second membrane comprises at least one method selected from the group consisting of drop coating, masking for spray coating, and dip coating to multiple depths.

In an embodiment of the seventh aspect, the system is configured to measure a current produced by at least one of the first sensor element or the second sensor element with substantial linearity at glucose concentrations of up to about 400 mg/dL in fluid with an oxygen concentration of less than about 0.6 mg/L.

In an eighth aspect, a sensor system is provided for continuous measurement of an analyte concentration in a host, the sensor system comprising a first sensor element configured to measure an analyte concentration and generate a first signal; a second sensor element configured to measure the analyte concentration and generate a second signal, the second sensor element having at least one characteristic different from the first sensor element; and sensor electronics configured to determine an analyte concentration value based on at least one of the first signal or the second signal.

In an embodiment of the eighth aspect, the sensor electronics are configured to estimate an analyte concentration value based on at least one of the first signal or the second signal and based on an estimation of a parameter.

In an embodiment of the eighth aspect, the sensor electronics are further configured to average or integrate the first signal and the second signal.

In an embodiment of the eighth aspect, the sensor electronics are further configured to assign a first weight to the first signal and assign a second weight to the second signal, wherein a magnitude of the first weight and a magnitude of the second weight are dependent on the estimation of the parameter.

In an embodiment of the eighth aspect, the parameter is associated with the analyte concentration.

In an embodiment of the eighth aspect, the parameter is associated with a time period of a sensor session.

In an embodiment of the eighth aspect, the parameter is associated with a presence of a level of an interferent.

In an embodiment of the eighth aspect, the parameter is associated with a concentration of oxygen.

In an embodiment of the eighth aspect, the first sensor element comprises a first membrane having a first hydrophilic component and a first hydrophobic component, wherein the second sensor element comprises a second membrane having a second hydrophilic component and a second hydrophobic component, and wherein the first sensor membrane and the second sensor membrane have a different hydrophilic to hydrophobic ratio.

In an embodiment of the eighth aspect, the first membrane comprises a first domain configured to reduce a flux of the analyte therethrough, wherein the second membrane comprises a second domain configured to reduce a flux of the analyte therethrough, and wherein the first domain and the second domain are different.

In an embodiment of the eighth aspect, the system further comprises a potentiostat configured to apply a first bias potential to the first sensor element and to apply a second bias potential to the second sensor element, wherein the first bias potential and the second bias potential are different.

In an embodiment of the eighth aspect, the first sensor element comprises a first membrane configured to reduce a flux of interferents therethrough, wherein the second sensor element comprises a second membrane configured to reduce a flux of interferents therethrough, and wherein interferent blocking characteristics of the first membrane and the second membrane are different.

In an embodiment of the eighth aspect, the first sensor element is further configured to monitor at least one levels of an interferent.

In a ninth aspect, a method is provided for processing data from a sensor system configured for continuous measurement of an analyte concentration in a host, the method comprising receiving a first signal, associated with an analyte concentration in a host, from a first sensor element; receiving a second signal, associated with the analyte concentration in the host, from a second sensor element, wherein the second sensor element hays at least one characteristic different from the first sensor element; and determining, using sensor electronics, an analyte concentration value based on at least one of the first signal or the second signal.

In an embodiment of the ninth aspect, determining the analyte concentration value is further based on an estimation of a parameter.

In an embodiment of the ninth aspect, determining the analyte concentration value comprises averaging or integrating the first signal and the second signal.

In an embodiment of the ninth aspect, averaging or integrating the first signal and the second signal comprises assigning a first weight to the first signal and assigning a second weight to the second signal, wherein a magnitude of the first weight and a magnitude of the second weight are dependent on the estimation of the parameter.

In an embodiment of the ninth aspect, the parameter is associated with the analyte concentration.

In an embodiment of the ninth aspect, the parameter is associated with a time period of a sensor session.

In an embodiment of the ninth aspect, the parameter is associated with a presence of a level of an interferent.

In an embodiment of the ninth aspect, the parameter is associated with a concentration of oxygen.

In an embodiment of the ninth aspect, the method further comprises applying a first bias potential to the first sensor element and a second bias potential to the second sensor element, wherein the first bias potential and the second bias potential are different.

In a tenth embodiment, a sensor system is provided for continuous measurement of an analyte concentration in a host, the sensor system comprising a first sensor element configured to measure analyte concentrations over a first time period of in vivo implantation; and a second sensor element configured to measure analyte concentrations over a second time period of in vivo implantation, wherein the first time period and the second time period are different.

In an embodiment of the tenth aspect, the first time period is associated with an initial period of in vivo implantation, wherein the second time period is associated with a second time period of in vivo implantation, and wherein the second period begins after the initial period of in vivo implantation has begun.

In an embodiment of the tenth aspect, the first time period and the second time period overlap partially, but not completely.

In an embodiment of the tenth aspect, the first time period and the second time period do not overlap.

In an embodiment of the tenth aspect, the first time period is from about day 1 post-implantation to about day 3 post-implantation, and wherein the second time period is from about day 2 post-implantation to about day 10 post-implantation.

In an embodiment of the tenth aspect, the first time period is from about day 1 post-implantation to about day 21 post-implantation, and wherein the second time period is from about day 10 post-implantation to about year 1 post-implantation.

In an embodiment of the tenth aspect, the sensor system is configured for implantation wholly in a tissue of a host.

In an embodiment of the tenth aspect, the sensor system is configured for transcutaneous placement through a skin of a host.

In an embodiment of the tenth aspect, the sensor system is configured for fluid communication with a vascular system of a host.

DETAILED DESCRIPTION

Figure 1A:
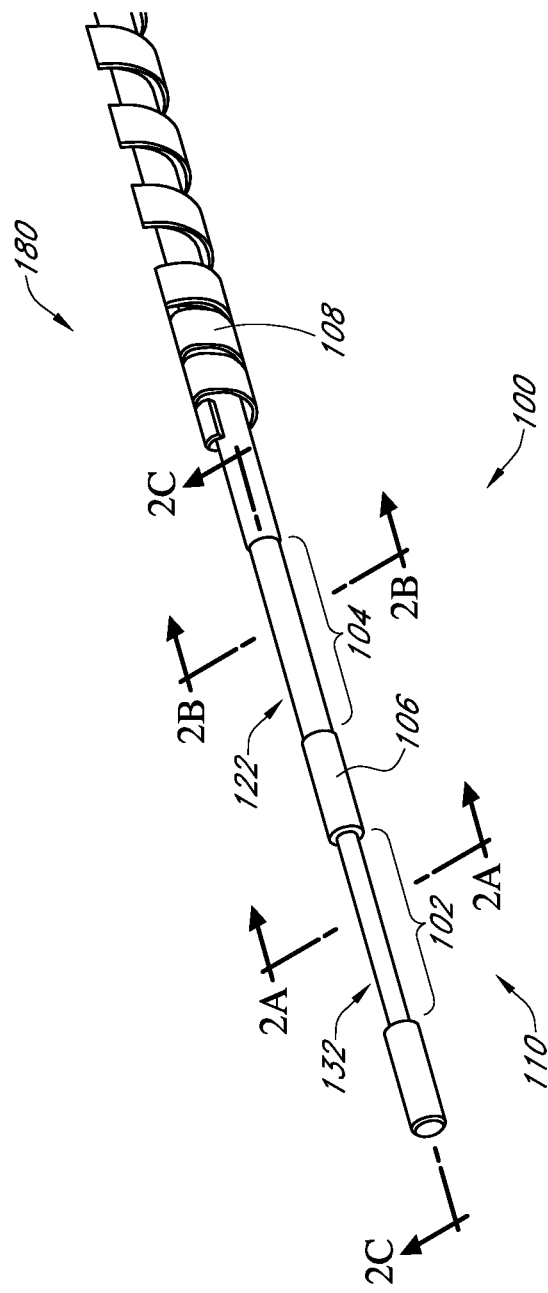
FIG. 1A is perspective view of one embodiment of a continuous analyte sensor.

In order to facilitate an understanding of the embodiments described herein, a number of terms are defined below.

The term "analyte," as used herein, is a broad term, and is to be given its ordinary and customary meaning to a person of ordinary skill in the art (and is not to be limited to a special or customized meaning), and refers without limitation to a substance or chemical constituent in a biological sample (e.g., bodily fluids, including, blood, serum, plasma, interstitial fluid, cerebral spinal fluid, lymph fluid, ocular fluid, saliva, oral fluid, urine, excretions or exudates). Analytes can include naturally occurring substances, artificial substances, metabolites, or reaction products. In some embodiments, the analyte for measurement by the sensing elements, devices, and methods is albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, metabolic markers, and drugs. However, other analytes are contemplated as well, including but not limited to acetaminophen, dopamine, ephedrine, terbutaline, ascorbate, uric acid, oxygen, d-amino acid oxidase, plasma amine oxidase, xanthine oxidase, NADPH oxidase, alcohol oxidase, alcohol dehydrogenase, pyruvate dehydrogenase, diols, Ros, NO, bilirubin, cholesterol, triglycerides, gentisic acid, ibuprophen, L-Dopa, methyl dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodo-thyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The terms "continuous" and "continuously," as used herein in reference to analyte sensing, are broad terms, and are to be given their ordinary and customary meaning to a person of ordinary skill in the art (and is not to be limited to a special or customized meaning), and refer without limitation to the continuous, continual, or intermittent (e.g., regular) monitoring of analyte concentration, such as, for example, performing a measurement about every 1 to 10 minutes.

The term "operably connected," as used herein, is a broad term, and is to be given its ordinary and customary meaning to a person of ordinary skill in the art (and is not to be limited to a special or customized meaning), and refers without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably connected" to the electronic circuitry.

The term "host" as used herein, is a broad term, and is to be given its ordinary and customary meaning to a person of ordinary skill in the art (and is not to be limited to a special or customized meaning), and refers without limitation to animals (e.g., humans) and plants.

The terms "electrochemically reactive surface" and "electroactive surface," as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The term "sensor element," as used herein, is a broad term, and is to be given its ordinary and customary meaning to a person of ordinary skill in the art (and is not to be limited to a special or customized meaning), and refers without limitation to the region or mechanism of a monitoring device responsible for the detection of a particular analyte.

The terms "raw data stream" and "data stream," as used herein, are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The phrase "distal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include an electrode covered by a membrane system having a diffusion resistance domain and an enzyme domain. If the electrode is deemed to be the point of reference and the diffusion resistance domain is positioned farther from the electrode than the enzyme domain, then the diffusion resistance domain is more distal to the electrode than the enzyme domain.

The phrase "proximal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include an electrode covered by a membrane system having a diffusion resistance domain and an enzyme domain. If the electrode is deemed to be the point of reference and the enzyme domain is positioned nearer to the electrode than the diffusion resistance domain, then the enzyme domain is more proximal to the sensor than the diffusion resistance domain.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (i.e., anisotropic) or provided as portions of the membrane.

The term "baseline," as used herein, is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal.

The term "sensitivity," as used herein, is a broad term, and is to be given its ordinary and customary meaning to a person of ordinary skill in the art (and is not to be limited to a special or customized meaning), and refers without limitation to an amount of electrical current produced by a predetermined amount (unit) of the measured analyte. For example, in one embodiment, a sensor has a sensitivity (or slope) of about 1 to about 300 picoAmps of current for every 1 mg/dL of glucose analyte.

The term "current density," as used herein, is a broad term, and is to be given its ordinary and customary meaning to a person of ordinary skill in the art (and is not to be limited to a special or customized meaning), and refers without limitation to an amount of electrical current per area produced by a predetermined amount (unit) of the measured analyte. For example, in one embodiment, a sensor has a sensitivity (or slope) of about 3 to about 1,000 picoAmps of current per $mm^2$ of electroactive surface, for every 1 mg/dL of glucose analyte.

Conventional continuous analyte sensors have typically lacked the capability to achieve a substantially consistent level of measurement accuracy across a physiologically relevant range. For instance, while some conventionally designed sensors have been capable of achieving high measurement accuracy in high-analyte-concentration environments, this measurement accuracy has typically been achieved by sacrificing measurement accuracy in low-analyte-concentration environments. Accordingly, designers of conventional continuous analyte sensors have typically had to choose between a sensor design that provided high measurement accuracy in a low analyte level environment, or alternatively a sensor design that provided high measurement accuracy in a high analyte level environment, but not a sensor design capable of providing high measurement accuracy in both low and high analyte level environments. Simply put, it has been a technical challenge to design a continuous analyte sensor capable of obtaining accurate measurements across a physiological relevant range.

Described herein is an improved sensor system with a plurality of sensor elements, in which each sensor element is designed to measure analyte concentration and to have a different characteristic, attribute, or configuration than the other sensor element(s) of the system. In some embodiments, sensor data from each of the plurality of different sensor elements is selectively used when a certain predetermined condition is present. The predetermined condition can relate to any of a variety of parameters, such as, oxygen concentration, time since initiation of the sensor session, presence of a certain level of interference activity, for example. The predetermined condition can also relate to analyte concentration. In certain embodiments, the continuous analyte sensor system comprises a plurality of sensor elements that are each configured to provide a preselected level of accuracy in two or more physiologically relevant ranges, so that the system can accurately measure an analyte concentration across a physiologically relevant range. In some embodiments, the plurality of sensor elements may provide the system with the capability of performing highly accurate measurements of glucose concentration in both hyperglycemic and hypoglycemic ranges.

Various methods for confirming accuracy of a sensor include, but are not limited to, the Clarke Error Grid, Parkes Error Grid, Continuous Glucose Error grid, Mean Absolute Relative Difference (MARD) analysis, and YSI (Yellow Springs Instrument) analysis. Some or all of these methods can be used to verify the accuracy of the sensor's measurements. In certain embodiments, the sensor's level of accuracy is verified by confirming that a high percentage (e.g., at least about 80%, at least about 85%, at least about 90%, at least about 95%, or at least about 98%) of its paired data points within zone A of the Clarke Error Grid. Alternatively, in other embodiments, the sensor's level of accuracy is verified by using a MARD analysis, such that the sensor's accuracy is confirmed with an MARD of about 30% or less, or about 25% or less, or about 20% or less, or about 15% or less, or about 10% or less, or about 5% or less. In yet other embodiments, the sensor's level of accuracy is verified by using YSI analysis, such that a large percentage of readings (e.g., about 70%, 75%, 80%, 85%, 90%, 95%, 98%, or more) are within about 20 mg/dL of a YSI reading.

Various housing arrangements for the sensor elements are contemplated. For example, in some embodiments, the plurality of sensor elements are housed within the same body, but in alternative embodiments the sensor elements are housed in different bodies. With embodiments in which a plurality of sensor elements are housed in the same body, in some of these embodiments, the sensor elements are physiologically connected or separated by a spacing.

Figure 1B:
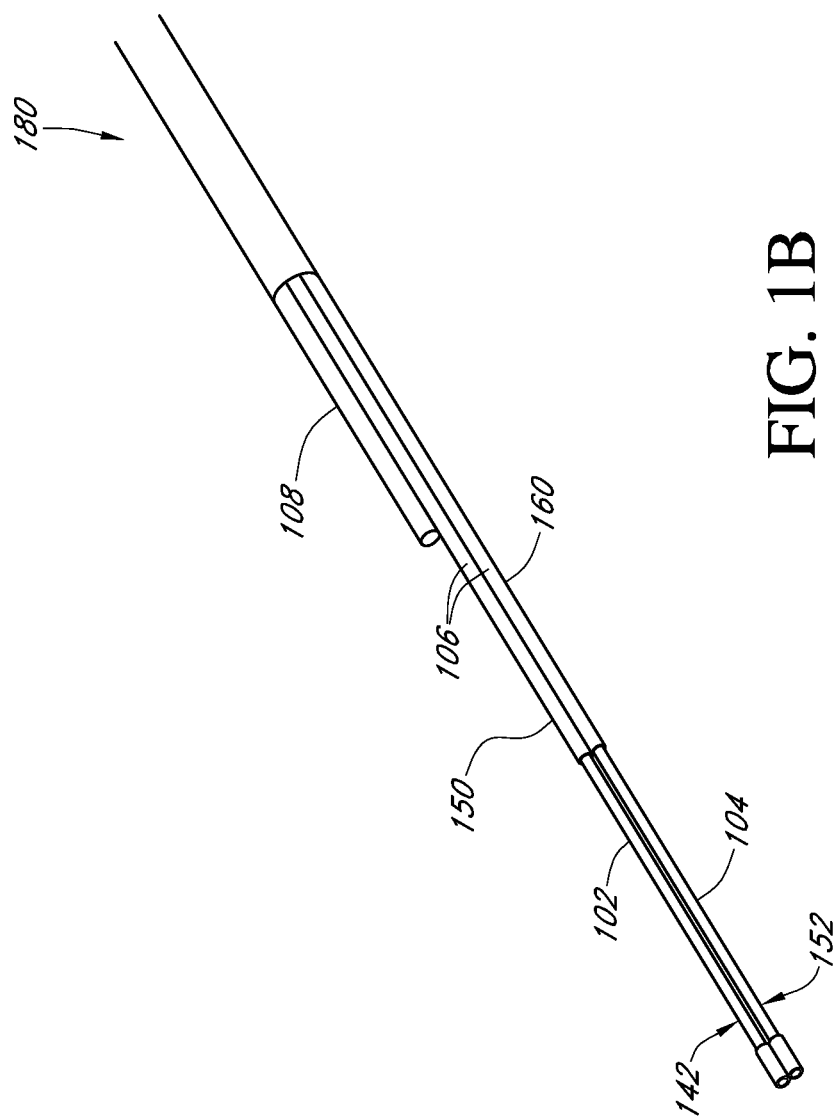
FIG. 1B is a perspective view of another embodiment of a continuous analyte sensor.

FIG. 1A provides a perspective view of one embodiment of a sensor system 180 and illustrates an in vivo portion of a working electrode 100 comprising two analyte sensor elements 102 and 104 and a reference electrode 108. The reference electrode 108 is used to provide a reference value for measuring the working electrode potential of the sensor elements 102, 104. In this particular embodiment, an insulator 106 is disposed between the two sensor elements 102 and 104, and between the sensor element 104 and the reference electrode 108, to provide necessary electrical insulation therebetween. In some embodiments, the insulator spacing separating the two sensor elements 102 and 104 may be minimized, so that the sensor elements 102 and 104 may both function under almost identical physiological conditions. In certain further embodiments, the insulator spacing can be from about 0.001 to about 100 microns, or from about 0.1 to about 50 microns, or from about 10 to about 25 microns. FIG. 1B provides a perspective view of another embodiment comprising a sensor system 180 having a first working electrode 150 comprising a first sensor element 102 and a second working electrode 160 comprising a second sensor element 104. Similar to the embodiment shown in FIG. 1A, the sensor system 180 also includes a reference electrode 108 for providing a reference value for measuring the working electrode potential of the sensor elements 102, 104. Both the first working electrode 150 and the second working electrode 160 comprise an insulator 106 that separates the sensor elements 102 and 104 from the reference electrode 108. Sensor element 102 is associated with a membrane 142, and sensor element 104 is associated with another membrane 152. In some embodiments, the thickness, composition, and/or structure of one or more layers (e.g., electrode, interference, or enzyme domains) of membrane system 142 differs from that of membrane system 152, but in other embodiments membranes 142, 152 may be substantially the same. Additional sensor systems and configuration are described in U.S. Provisional Application No. 61/222,751 filed Jul. 2, 2009 and U.S. patent application Ser. No. 12/829,296, filed Jul. 1, 2010, and entitled "ANALYTE SENSORS AND METHODS FOR MANUFACTURING SAME," each of which is incorporated by reference herein in its entirety.

A wide variety of sensor configurations are contemplated with respect to sensor placement. For example, in some embodiments, the sensor is configured for transdermal (e.g., transcutaneous) placement, but in other embodiments the sensor is configured for intravascular placement, subcutaneous placement, intramuscular placement, or intraosseous placement. The sensor may use any method to provide an output signal indicative of the concentration of the analyte of interest; these methods may include, for example, invasive, minimally invasive, or non-invasive sensing techniques.

The output signal associated with the analyte concentration of the host is typically a raw signal used to provide a useful value of the analyte of interest to a user (e.g., a patient or physician) using the device. Accordingly, appropriate smoothing, calibration, or evaluation methods can be applied to the signal or system as a whole to provide relevant and acceptable estimated analyte data to the user.

It is contemplated that the sensor may use any of a wide variety of known suitable detection methods. These methods may include, but are not limited to, enzymatic, chemical, physical, electrochemical, immunochemical, optical, radiometric, calorimetric, protein binding, microscale methods of detection, and the like. Additional description of analyte sensor configurations and detection methods can be found, e.g., in U.S. Patent Publication No. US-2007-0213611-A1, U.S. Patent Publication No. US-2007-0027385-A1, U.S. Patent Publication No. US-2005-0143635-A1, U.S. Patent Publication No. US-2007-0020641-A1, U.S. Patent Publication No. US-2007-0020641-A1, U.S. Patent Publication No. US-2005-0196820, U.S. Pat. Nos. 5,517,313, 5,512,246, 6,400,974, 6,711,423, 7,308,292, 7,303,875, 7,289,836, 7,289,204, 5,156,972, 6,528,318, 5,738,992, 5,631,170, 5,114,859, 7,273,633, 7,247,443, 6,007,775, 7,074,610, 6,846,654, 7,288,368, 7,291,496, 5,466,348, 7,062,385, 7,244,582, 7,211,439, 7,214,190, 7,171,312, 7,135,342, 7,041,209, 7,061,593, 6,854,317, 7,315,752, and 7,312,040. Although the illustrated sensor configurations and associated text describe a few methods for forming a sensor, any of a variety of known sensor configurations can be employed with the analyte sensor system, such as, for example, U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,103,033 to Say et al., U.S. Pat. No. 6,512,939 to Colvin et al., U.S. Pat. No. 6,424,847 to Mastrototaro et al., and U.S. Pat. No. 6,424,847 to Mastrototaro et al. The sensors described in the above-referenced patents are not inclusive of all applicable analyte sensors; rather, the disclosed embodiments can be applicable to any of a variety of analyte sensor configurations. The description of the embodiments herein, for example the membrane system described below, can be implemented not only with in vivo sensors, but also with in vitro sensors, such as blood glucose meters (SMBG), and any other known analyte sensors.

As described above, in some embodiments, the sensor system comprises a plurality of sensor elements, each or some of which are configured to measure different ranges of analyte concentration. For example, the sensor system may include a first sensor element configured to accurately measure analyte concentration in a first range of analyte concentrations and a second sensor element configured to accurately measure analyte concentration in a second range of analyte concentrations. In some embodiments, the sensor system is configured to measure glucose concentration over a range of from about 30, 40, 50, 60, 70, or 80 mg/dL to about 200, 250, 300, 350, 400, 450, 500, 550 or 600 mg/dL. As described above, in some embodiments, the sensor system includes a plurality of sensor elements configured to measure different analyte concentration ranges, each of which comprises a portion of the physiologically relevant range. In some of these embodiments, the different ranges do not overlap, but in other embodiments, the ranges overlap, either partially or entirely. By way of example, in one embodiment, the sensor system comprises a first sensor element configured to measure a glucose concentration of from about 30 mg/dL to about 120 mg/dL and a second sensor element configured to measure a glucose concentration of from about 80 mg/dL to about 400 mg/dL. In this particular embodiment, there is a partial overlapping of measurement ranges of from about 80 mg/dL to about 120 mg/dL. In alternative embodiments, other measurement ranges are contemplated for each of the plurality of sensor elements. For example, in some embodiments, the first sensor element is configured to measure a glucose concentration of from about 30 mg/dL to about 120 mg/dL, or from about 40 mg/dL to about 100 mg/dL, and the second sensor element is configured to measure a glucose concentration of from about 60 mg/dL to about 500 mg/dL, or from about 90 mg/dL to about 450 mg/dL.

Although the examples provided above describe a sensor system comprising two sensor elements, it is contemplated that the sensor system can comprise any number of sensor elements. In some embodiments, the plurality of sensor elements may each be tuned to measure at a particular analyte concentration range, tuned to measure at a particular time period during a sensor session, and/or to tuned to measure at any particular range of any of a variety of parameters (e.g., parameters relating to concentration of oxygen, concentration of a interferent, etc.). For instance, in some embodiments, the sensor system comprises three sensor elements configured to measure a first range, a second range, and a third range, e.g., with a first sensor element associated with a range of about 30-90 mg/dL, a second sensor element associated with a range of about 80-160 mg/dL, and a third sensor element associated with a range of about 140-400 mg/dL. In other embodiments, the sensor system is provided with 4, 5, 6, 7, 8, 9, 10, 20, 40, or more sensor elements.

As used herein, language associating sensor measurement or output of analyte concentration to a particular range of analyte concentrations, particular range of time, or any other range corresponding to a parameter or condition, should not be construed as precluding the sensor element from measuring outside the particular range described or from having its signal used to form an estimation of an analyte concentration value (e.g., estimation by using a weighted average or weighted sum of a plurality of signals). Rather, such language should be construed to mean that the sensor element is configured to be tuned (with respect to measurement accuracy) to a particular range, such that all or a weighted portion of the sensor output of analyte concentrations in that particular range comes from the sensor element particularly tuned thereto. By way of example, in a sensor system with a first sensor element and a second sensor element, each sensor element may have a different configuration and be tuned to measure analyte concentration within a preselected analyte concentration range (e.g., high glucose concentration range vs. low glucose concentration range). Even though each of the two sensor elements may be capable of measuring at any analyte concentration, the exemplary sensor system is configured to provide output to a user from the first sensor element, second sensor element, or both, based, at least in part, on the analyte concentration range that the first or second sensor element is particularly tuned for. In addition, as used herein, the phrase "accurately measure," or the like, should be construed as referring to a level of accuracy that provides clinically useful analyte measurements.

In some of these embodiments, the sensitivity or current density (i.e., sensitivity divided by surface area of the electroactive surface) of one or more of the sensor elements is substantially higher than the sensitivities or current densities of other sensor elements, but in other embodiments, the sensitivities or current densities of the sensor elements are substantially equal. In some embodiments, the sensor system includes a first sensor element having a first sensitivity and a second sensor element having a second sensitivity, wherein the first sensitivity is higher than the second sensitivity. In some embodiments, the first sensitivity is from about 1 pA/mg/dL to about 100 pA/mg/dL, or from about 1 pA/mg/dL to about 25 pA/mg/dL, and the second sensitivity is from about 20 pA/mg/dL to about 300 pA/mg/dL, or from about 50 pA/mg/dL to about 100 pA/mg/dL. In some embodiments, the sensor system includes a first sensor element having a first current density and a second sensor element having a second current density, wherein the first current density is higher than the second current density. In some of these embodiments, the current density of the first element is from about 3 pA/mg/dL/mm$^2$ to about 325 pA/mg/dL/mm$^2$, or from about 3 pA/mg/dL/mm$^2$ to about 85 pA/mg/dL/mm$^2$, and the current density of the second element is from about 65 pA/mg/dL/mm$^2$ to about 1,000 pA/mg/dL/mm$^2$, or from about 165 pA/mg/dL/mm$^2$ to about 1,700 pA/mg/dL/mm$^2$.

In some embodiments, the sensor element with the higher sensitivity or higher current density is used to measure or provide output at low glucose concentration ranges, while the sensor element with the lower sensitivity or lower current density is used to measure or provide output at high glucose concentration ranges. Advantageously, in some embodiments, improved glucose concentration measurement accuracy at both low and high glucose levels is achieved by configuring the first sensor element to have a higher sensitivity or higher current density and the second to have a lower sensitivity or lower current density.

In some embodiments, the sensor elements each have a different bias potential applied against it by a potentiostat. An increased bias potential applied against a sensor element may not only facilitate the oxidization and measurement of $H_2O_2$, but may also facilitate the oxidization of water or other electroactive species. In one example, the bias setting is increased by about 0.05 V to about 0.4 V above what is necessary for sufficient $H_2O_2$ measurements. By increasing the bias potential, an electrolysis reaction of water (and possibly other electroactive species) may be carried out, whereby oxygen is produced at the electroactive surface of sensor element. The oxygen produced then diffuses in various directions, including up to the glucose oxidase directly above the electroactive surface. This production of oxygen increases sensor function, particularly in low oxygen environments.

Referring back to embodiments described above, in one further embodiment, the sensor system comprises a first sensor element configured with a first bias setting (for example, +0.6V) for measuring a signal only from the product of the enzyme reaction, and a second sensor element configured with a second bias setting (for example, +1.0V) that oxidizes and measures water or other electroactive species. In this embodiment, the first sensor element is configured to measure at low analyte ranges, where the oxygen-to-glucose molar ratio is high, and the second element is configured to measure at high analyte ranges, where the oxygen-to-glucose molar ratio is low and where additional oxygen can be helpful for preventing a molar excess of glucose relative to oxygen.

In some embodiments, the sensor elements each have different analyte-related to non-analyte-related signal ratios. For example, in one embodiment, wherein the sensor system includes first and second sensor elements, and wherein the first sensor element has a higher sensitivity or higher current density than the second sensor element, the first sensor element also has higher analyte-related to non-analyte-related signal ratio than the second sensor element. Advantageously, in some embodiments, the combination of a higher sensitivity or higher current density and a higher analyte-related to non-analyte-related signal ratio further improves measurement accuracy at low analyte levels. An increase or decrease of the analyte-related to non-analyte-related signal ratio may be obtained by modifying membrane properties (e.g., composition, thickness, etc.).

As described elsewhere herein in regard to membrane systems, it is contemplated that in some embodiments, the sensor system has a plurality of sensor elements, in which one or more of the sensor elements are configured to have a different membrane system (i.e., with different membrane properties) than the other sensor element(s). In some embodiments, the plurality of sensor elements each comprises a membrane with a hydrophilic component and a hydrophobic component, with the membrane of each sensor element having a different hydrophilic component to hydrophobic component ratio than the ratio(s) of the membrane(s) of other sensor element(s). By altering the hydrophilic component to hydrophobic component ratio (as determined by weight), membrane properties can be changed. These membrane property changes can include changes to, for example, permeability of analyte, sensitivity to analyte, permeability of interferents, sensitivity to interferents, permeability to oxygen, expected sensor life, accuracy at certain periods during a sensor session, etc.

In addition, changing the hydrophilic component to hydrophobic component ratio can also change the sensor run-in-time (i.e., the time between the insertion of the sensor subcutaneously and stabilization of the sensor). It has been found that an increase in this ratio (i.e., larger amounts of the hydrophilic component than the hydrophobic component) can substantially reduce run-in time. While not wishing to be bound by theory, it is believed that this phenomenon may be attributed at least in part to faster hydration of membranes having a greater proportion of hydrophilic components, when the sensor is inserted into the patient and contacts a biological sample. In certain embodiments, the sensor system may comprise one sensor element with a reduced run-in-time (e.g., about 0.1 hour, 0.2 hour, 0.3 hour, 0.4 hour, 0.5 hour, 1 hour, 2 hours, 3 hours, 4, hours, or 6 hours) that is tuned to an early portion of the sensor session and other sensor element(s) that are tuned to other portions of the sensor session. In further embodiments, the sensor element configured with the reduced run-in-time may be used to calibrate the other sensor elements.

There typically exists a molar excess of glucose relative to the amount of oxygen in blood. To achieve accurate sensor measurements of glucose concentration, the amount of oxygen present for the glucose-oxidase-catalyzed reaction has to be greater than that of glucose. Otherwise, an oxygen limiting reaction, instead of a glucose limiting reaction, may occur, especially at high glucose concentration levels. More specifically, when a glucose-monitoring reaction is oxygen limited, the glucose sensor's linearity may be lost at concentrations of glucose within a physiologically relevant range. In order to achieve high sensitivity or high current density, sensor elements can be formed with a membrane that permits a greater flux of glucose molecules into the enzyme layer (which may comprise glucose oxidase) of the membrane, than sensor elements designed for low sensitivity or low current density. To overcome potential issues relating to a molar excess of glucose relative to oxygen in a high sensitivity or high current density sensor element, in some embodiments, the sensor system is designed to comprise a plurality of sensor elements, each of which is configured to have different membrane characteristics, with respect to oxygen permeability and/or glucose permeability. In some embodiments, each of the plurality of sensor elements may have a different sensitivity or current density. For example, in one embodiment, the sensor system comprises a first sensor element configured with a high sensitivity or high current density and a second sensor element configured with a low sensitivity or low current density. It has been found that high glucose sensitivity sensor elements typically perform worse in lower oxygen environments than the low glucose sensitivity sensor element. Thus, in certain analyte concentration levels where oxygen is a limiting reactant or in low oxygen environments, the sensor system can be configured to accept data from the low sensitivity or low current density sensor element, instead of the high sensitivity or high current density sensor element. Alternatively, data from the high sensitivity or high current density sensor element may still be accepted, but accorded less weight than data from the low sensitivity or low current density sensor element.

As described elsewhere herein, in some embodiments, comparison and analysis is performed on signals. The comparison and analysis can include integrating or averaging signals from a plurality of sensor elements. In some embodiments, the sensor electronics may be configured to accord less (or no) weight to a high sensitivity sensor element, as compared to a low sensitivity sensor element, in environments associated with low oxygen and high glucose concentration. Conversely, the sensor electronics may be configured to accord more weight to the high sensitivity sensor element in environments associated with high oxygen and low glucose concentration. As an alternative to weighting, the sensor electronics may be configured to poll sensor data from the low glucose sensitivity sensor only when an environment associated with a low oxygen environment is detected.

In some embodiments, signals received from the two sensor elements can be compared and analyzed to provide information not only about glucose concentration, but information about other parameters that can affect sensor performance. For example, during a sensor session, if the oxygen level near the sensor elements diminishes below a certain level, the high sensitivity sensor element may no longer be accurate. Under these conditions, the high sensitivity sensor may become noisy and thus become less accurate, while the low sensitivity sensor element can continue to measure accurately. Accordingly, in some embodiments in which comparison and analysis of signals is made by integrating or averaging signals from a plurality of sensor elements, the sensor electronics may be configured to accord less (or no) weight to a high sensitivity sensor element, as compared to a low sensitivity sensor element, in environments associated with low oxygen and high glucose concentration. Conversely, the sensor electronics may be configured to accord more weight to the high sensitivity sensor element in environments associated with high oxygen and low glucose concentration. As an alternative to weighting, the sensor electronics may be configured to poll sensor data from the low glucose sensitivity sensor only when an environment associated with a low oxygen environment is detected.

In some embodiments, the noise that may be present in data from a high sensitivity sensor element (e.g., one in the presence of a low oxygen environment) may provide an indication that a low glucose sensitivity sensor is approaching an environment in which it may also become inaccurate as well. Accordingly, the sensor electronics may be configured to monitor, on the high sensitivity sensor element, a noise pattern that corresponds to a low oxygen environment.

Following detection of the noise pattern, the sensor electronics can be instructed to poll data from the low sensitivity only, or alternatively adjust the weight accorded to the high sensitivity sensor with respect to the low sensitivity sensor.

While not wishing to be bound by theory, it is believed that oxygen availability typically decreases with time during the age of a sensor, as the amount of oxygen that can be transported across the membrane of a sensor element diminishes. While not wishing to be bound by theory, it is believed that this phenomenon may be attributed at least in part to the body's response to a foreign object (e.g., a continuous glucose sensor), whereby barrier cells are formed surrounding the sensor elements. In turn, the barrier cells reduce or completely block the transport of oxygen across the membrane of the sensor elements. In some embodiments, the sensor system is formed with a high sensitivity or high current density sensor element that provides greater accuracy during a large duration of the sensor system's life, and a low sensitivity or low current density sensor element that provides better low oxygen performance, and thus can be used near the end of the sensor system's life.

In some embodiments, the sensor system comprises a plurality of sensor elements used to continuously provide sensor data after insertion of the sensor, even during time periods which may be problematic for conventional sensors. In some of these embodiments, the sensor system comprises a first sensor element and a second sensor element, each with different membrane properties. The first sensor element is tuned to measure analyte concentration during a first period, such as an initial time period after sensor implantation (e.g., during about the first 0.1 hour, 0.2 hour, 0.5 hour. 0.75 hour, 1 hour, 2 hours, 3 hours, 6 hours, 12 hours, 1 day, 2 days, 3 days, 4 days, 5 days, 6 days, or 7 days post-insertion). In certain embodiments, the first sensor element is designed with a particular membrane (e.g., a membrane that hydrates quickly after insertion into interstitial fluid) that is tuned for accuracy during the initial period after sensor insertion. The second sensor element is tuned to measure analyte concentration during a second time period (e.g., after about 0.2 hour, 0.5 hour, 0.75 hour, 1 hour, 2 hours, 3 hours, 6 hours, 12 hours, 1 day, 2 days, 3 days, 4, days, 5 days, 7 days, 2 weeks, or 1 year post-insertion), where the second period begins after the initial period begins. In some embodiments, the time periods of the different sensor elements overlap. As described herein elsewhere in more detail, by varying the membrane properties of a sensor element, sensor elements can be tuned to measure accurately over a specific time period. In some embodiments, the time periods overlap partially, but in other embodiments, there is no overlap of time periods. In one example of a sensor system with partial overlap of time periods, the first time period is from about hour 0.2 to about day 3 post-insertion, and the second time period is from about hour 6 to about day 10 post-insertion. Thus, in this particular example, there is partial overlap between hour 6 and day 3 post-insertion. Other examples include, but are not limited to, a sensor system having the first time period of from about day 1 to about day 21, and a second time period of from about day 10 to about year one. In yet another embodiment, the time period of one sensor may completely overlap the time period of another sensor. In one example of a sensor system with complete overlap of time periods, the first time period is from about hour 0.5 to about day 2, the second time period is from about hour 6 to about day 10, and the third time period is from about day 3 to about day 10. In this particular example, the second time period completely overlaps the third time period. In some embodiments, the second sensor element tuned to measure at a later time period may be formed with a robust biointerface to create strong vascularized tissue ingrowth, thereby providing more durability, but also a longer break in time. By having a plurality of sensor elements tuned to different time periods, the sensor system is capable of continuously and accurately measuring analyte concentrations across a wide range of time periods.

Figure 2B:
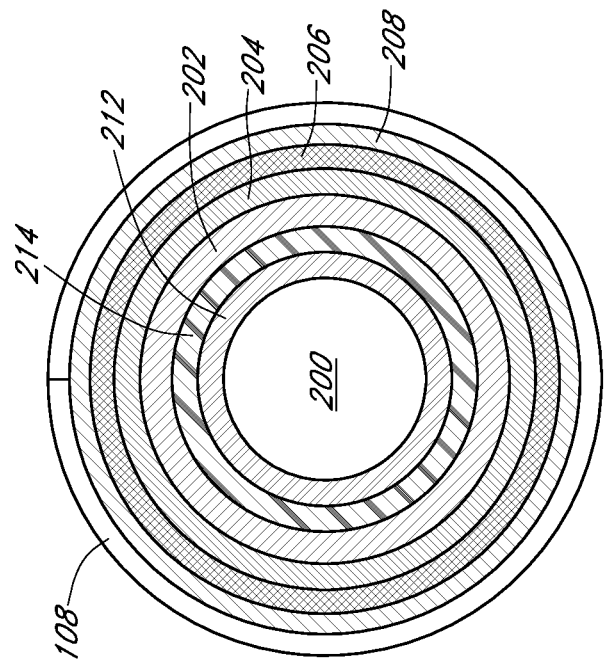
FIG. 2B is a cross-sectional view through the analyte sensor of FIG. 1A on line 2B-2B, illustrating one embodiment of the membrane system.
Figure 2A:
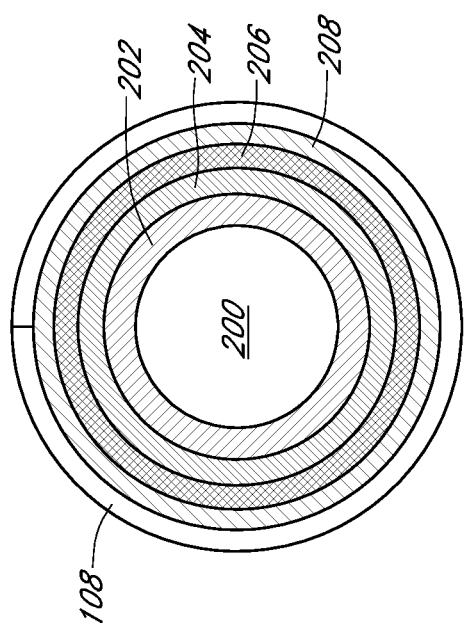
FIG. 2A is a cross-sectional view through the analyte sensor of FIG. 1A on line 2A-2A, illustrating one embodiment of the membrane system.

In some embodiments, the sensor includes a membrane system comprising a single layer deposited onto the electroactive surfaces of the sensor, wherein the single layer includes one or more functional domains (e.g., distinct portions). In other embodiments, however, the membrane system includes two or more deposited layers, each of which is configured to perform different functions. For example, FIG. 2A is a cross-sectional view through one embodiment of the sensor element 102 of FIG. 1A on line 2A-2A, illustrating one exemplary embodiment of a membrane system 132 covering an elongated conductive body 200. The term "elongated conductive body" as used herein is a broad term, and is to be given its ordinary and customary meaning to a person of ordinary skill in the art (and is not to be limited to a special or customized meaning), and refers without limitation to an elongated body formed at least in part of a conductive material and includes any number of coatings formed thereon. By way of example, an "elongated conductive body" may be in the form of a bare elongated core (e.g., a metal wire, a wire formed of a conductive polymer, a planar substrate formed of a non-conductive material) or an elongated core covered (e.g., coated, plated, cladded, etc.) with one, two, three, four, five, or more layers or domains of material that may be conductive or non-conductive.

Figure 2C:
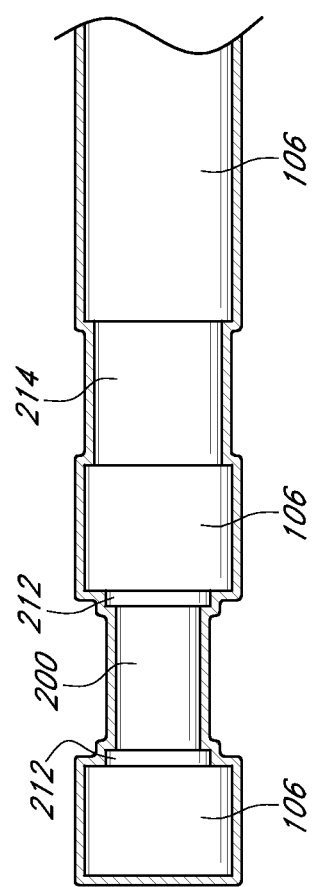
FIG. 2C is a cross-sectional view through the analyte sensor of FIG. 1A on line 2C-2C, illustrating one embodiment of the membrane system.

As illustrated in FIG. 2A, the membrane system 132 comprises a plurality of domains, including an electrode domain 202, an interference domain 204, an enzyme domain 206, and a diffusion resistance domain 208. FIG. 2B is a cross-sectional view through one embodiment of the sensor element 104 of FIG. 1A on line 2B-2B, illustrating one exemplary embodiment of a membrane system 122 covering an elongated conductive body 200 covered by an insulating domain 212 and a conductive domain 214. As illustrated in FIG. 2B, similar to the membrane system 132 associated with sensor element 102, in one embodiment, the membrane system 122 associated with sensor element 104 also comprises an electrode domain 202, an interference domain 204, an enzyme domain 206, and a diffusion resistance domain 208. FIG. 2C illustrates a cross-sectional view through line 2C-2C of FIG. 1A. In some embodiments, the thickness, composition, and/or structure of one or more layers (e.g., electrode, interference, or enzyme domains) of membrane system 132 differs from that of membrane system 122.

Although not shown, it is contemplated that this particular embodiment can also include a high oxygen solubility domain, a biointerface domain, or a bioprotective domain, such as is described in more detail in U.S. Patent Application Publication No. US-2005-0245799-A1, U.S. Patent Application Publication No. US-2009-0247856-A1, and U.S. Patent Application Publication No. US-2009-0247855-A1, and such as are described in more detail below.

During manufacturing, the membrane system can be deposited on the exposed electroactive surfaces using known thin film techniques including, but not limited to, conventional vapor deposition, spraying, electro-depositing, dipping, and the like. For example, in some embodiments, the domains are deposited by dipping the sensor into a solution and drawing out the sensor at a speed that provides the desired domain thickness. As another example, the domains are deposited by spraying a solution onto the sensor for a period of time which provides the desired domain thickness. In other embodiments, a combination of different deposition techniques is used for the different domains being deposited. For example, in one embodiment, dipping processes are used to deposit the electrode and enzyme domains onto the electrode, whereas a spraying process is used to deposit the diffusion resistance domain.

In alternative embodiments, other vapor deposition processes (e.g., physical or chemical vapor deposition processes) are also used, in addition to or in place of the above-mentioned techniques, to provide one or more of the insulating or membrane layers. These processes include, but are not limited to, ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method.

In some embodiments, one or more domains of the membrane system is formed from one or more materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, polyamides, polyimides, polystyrenes, cellulosic polymers, polysulfones and block copolymers thereof including, for example, di-block, tri-block, alternating, random and graft copolymers. U.S. Patent Application Publication No. US-2005-0245799-A1 describes biointerface and membrane system configurations and materials that can be employed in connection with the membrane systems of certain embodiments.

In some embodiments, the membrane system comprises an electrode domain. Providing the electrode domain 202 ensures that an electrochemical reaction occurs between the electroactive surfaces of the working electrode and the reference electrode, and thus the electrode domain may be situated more proximal to the electroactive surfaces than the interference or enzyme domain. In some of these embodiments, the electrode domain includes a coating that maintains a layer of water at the electrochemically reactive surfaces of the sensor. In other words, the presence of the electrode domain provides an environment between the surfaces of the working electrode and the reference electrode which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain includes a hydrophilic polymer film (e.g., a flexible, water-swellable, hydrogel) having a "dry film" thickness of from about 0.05 microns or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 3, 2.5, 2, or 1 microns, or less, to about 3.5, 4, 4.5, or 5 microns or more. "Dry film" thickness refers to the thickness of a cured film cast from a coating formulation by standard coating techniques.

In some embodiments, the electrode domain is formed of a curable mixture of a urethane polymer and a hydrophilic polymer. In certain embodiments, coatings are formed of a polyurethane polymer having carboxylate or hydroxyl functional groups and non-ionic hydrophilic polyether segments, wherein the polyurethane polymer undergoes aggregation with a water-soluble carbodiimide (e.g., 1-ethyl-3-(3-dimethylaminopropyl)carbodiimide (EDC)) in the presence of polyvinylpyrrolidone and cured at a moderate temperature of, e.g., about 50° C.

In some embodiments, the electrode domain is formed from one or more hydrophilic polymers (e.g., a polylactone, a polyimide, a polylactam, a functionalized polyamide, a functionalized polylactone, a functionalized polyimide, a functionalized polylactam or a combination thereof) that renders the electrode domain substantially more hydrophilic than an overlying domain, (e.g., interference domain, enzyme domain). In some embodiments, the electrode domain is formed substantially entirely or primarily from a hydrophilic polymer. In some embodiments, the electrode domain is formed substantially entirely from poly-N-vinylpyrrolidone (PVP). In some embodiments, the electrode domain is formed entirely from a hydrophilic polymer. Useful hydrophilic polymers include but are not limited to poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers may be desirable in some embodiments. In some embodiments, the hydrophilic polymer(s) is not crosslinked, but in other embodiments, crosslinking is performed. In such embodiments, crosslinking can be promoted by, e.g., adding a crosslinking agent, such as but not limited to 1-ethyl-3-(3-dimethylaminopropyl)carbodiimide, or by irradiation at a wavelength sufficient to promote crosslinking between the hydrophilic polymer molecules. While not wishing to be bound by theory, it is believed that crosslinking creates a more tortuous diffusion path through the domain. Although an independent electrode domain is described herein, in some embodiments sufficient hydrophilicity is provided in the interference domain or enzyme domain (the domain adjacent to the electroactive surfaces) so as to provide for the full transport of ions in the aqueous environment (e.g., without a distinct electrode domain). In these embodiments, an electrode domain may not be necessary.

In some embodiments, the sensor system comprises a plurality of sensor elements, each with different electrode domain properties. For example, in one embodiment, one of the plurality of sensor elements may be designed to allow for quick hydration of the electrode domain following insertion of the sensor into the body. It has been found that fast hydration of the electrode domain may lead to a reduction in run-in time of the sensor.

It is contemplated that in some embodiments, the membrane system is provided with an optional interference domain, also referred to as an interference layer. The interference domain substantially reduces the flux of one or more interferents into the electrochemically reactive surfaces. The interference domain may be configured to be much less permeable to one or more of the interferents than to the measured species, e.g., the product of an enzymatic reaction that is measured at the electroactive surface(s), such as $H_2O_2$, for example. In turn, the reduction of interferent permeability corresponds to a reduction or a blocking of artificial signals. Some known interferents for a glucose sensor include acetaminophen, lidocaine, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid, for example. Advantageously, the interference domain contemplated in certain embodiments is configured to improve interferent blocking in certain key ranges (e.g., a hypoglycemic range), where a flux of interferents substantially exaggerates the response signal, thereby leading to false or misleading results. This can be achieved by modifying the thickness or composition of the interference domain to obtain an interference domain with the desired properties. Use of an interference domain in the membrane may result in longer membrane diffusion times (e.g., 1 minute, 5 minutes, 10 minutes, 20 minutes, 30 minutes or more) for the measured species, because of the interference layer's additional thickness to the membrane. Use of the interference domain may also result in increased startup times (e.g., 30 minutes, 1 hour, 3 hours, 6 hours, 9 hours, or 12 hours), due to the additional time required for the sensor to hydrate and break in. Accordingly, by building a sensor with two or more different sensor elements, each selected for different measurement ranges, properties, or time periods for start up, the sensor system can be tuned or adjusted with respect to measurement accuracy across a physiological relevant range of glucose concentrations, start up time, diffusional time lags, and the like. In some embodiments, the sensor system comprises a first sensor element and a second sensor element, each with different interference domain properties. For example, in some embodiments, the first sensor element is configured to measure glucose concentrations in hypoglycemic ranges by being formed with an interference layer with an increased thickness to substantially reduce or block the flux of interferents. In contrast, the second sensor element is configured to measure glucose concentrations in hyperglycemic ranges by being formed without an interference layer, or alternatively by being formed with an interference layer with decreased thickness.

In one embodiment, the interference domain is formed from one or more cellulosic derivatives. Cellulosic derivatives include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose. While cellulosic derivatives are used in some embodiments, other polymeric polysaccharides having similar properties to cellulosic derivatives can also be employed. Descriptions of cellulosic interference domains can be found in U.S. Patent Application Publication No. US-2006-0229512-A1, U.S. Patent Application Publication No. US-2007-0173709-A1, U.S. Patent Application Publication No. US-2006-0253012-A1 and U.S. Patent Application Publication No. US-2007-0213611-A1.

In some embodiments, other polymer types that can be utilized as a base material for the interference domain include, but are not limited to, polyurethanes, polymers having pendant ionic groups, and polymers having controlled pore size. In one such alternative embodiment, the interference domain includes a thin, hydrophobic membrane that is non-swellable and restricts diffusion of high molecular weight species. The interference domain in certain embodiments is permeable to relatively low molecular weight substances, such as hydrogen peroxide, but also restricts the passage of higher molecular weight substances, including glucose and ascorbic acid. Other systems and methods for reducing or eliminating interference species that can be applied to the membrane system are described in U.S. Pat. No. 7,074,307, U.S. Patent Application Publication No. US-2005-0176136-A1, U.S. Pat. No. 7,081,195, and U.S. Patent Application Publication No. US-2005-0143635-A1. In some alternative embodiments, a distinct interference domain is not included in the membrane system or is functionally combined with another layer. In some embodiments, the interference domain is deposited either directly onto the electroactive surfaces of the sensor or onto the distal surface of the electrode domain. It is contemplated that in some embodiments the thickness of the interference domain is from about 0.01 microns or less to about 20 microns or more. In some of these embodiments, the thickness of the interference domain is from about 0.01, 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. In some of these embodiments, the thickness of the interference domain is from about 0.2, 0.4, 0.5, or 0.6, microns to about 0.8, 0.9, 1, 1.5, 2, 3, or 4 microns.

In some embodiments, the sensor system comprises a plurality of sensor elements, each with different interference domain properties. It has been found that certain interference domains lack completely precise specificity with respect to interferents. In other words, with certain interference domains, the membrane not only reduces the flux of interferents, but also reduces the flux of glucose or measured species such as hydrogen peroxide generated from an enzyme-catalyzed reaction. In these embodiments, having an interference domain that substantially reduces the flux of an interferent may result in a sensor element with decreased sensitivity and a lower signal level than an equivalent sensor element without the interference domain. In view of the tradeoff that exists in certain interference domains between sensor sensitivity and interference blocking capability, it is contemplated that in certain embodiments, the sensor system may comprise a plurality of sensor elements, with each having different levels of interference blocking capabilities and/or having specificity for different interferents. Alternatively or additionally, the plurality of sensor elements may each have different specificity for different interferents. In one exemplary embodiment, the sensor system may comprise a first sensor element that has an interference domain specifically designed to substantially reduce (or block) the flux of a certain interferent (e.g., acetaminophen), a second sensor element that has a different interference domain specifically designed to substantially reduce (or block) the flux of another interferent (e.g., uric acid), a third sensor element that has yet another different interference domain specifically designed to substantially reduce (or block) the flux of yet another interferent (e.g., ascorbic acid), and a fourth sensor element that has no interference domain.

Detection of an elevated level of one or more interferents may be obtained by comparing signals associated with the different sensor elements. In certain embodiments, the processor module may be programmed to identify the presence of interferents by comparing sensor data with certain data patterns known to correspond to the presence of interferents. Upon detection of elevated levels of one or more interferents, processing of the plurality of data streams associated with their respective plurality of sensor elements may be adjusted. For example, in embodiments in which weighted averages or weighted sums are used to estimate analyte concentration value, sensor data associated with the sensor element configured with a higher interferent blocking ability may be accorded more weight, and sensor data associated with the sensor element(s) without or with minimal interferent blocking ability may be accorded less (or no) weight. Alternatively or additionally, a different filtering algorithm may be used on the sensor data, the sensor system may stop displaying data to the user if the interference level exceeds a certain threshold, and/or an alert or alarm may be triggered to prompt the user to take certain actions (e.g., to perform additional calibrations).

In some embodiments, the membrane system further includes an enzyme domain 206 disposed more distally from the electroactive surfaces than the interference domain; however other configurations are also contemplated. In some embodiments, the enzyme domain provides an enzyme to catalyze the reaction of the analyte and its co-reactant, as described in more detail below. In the some embodiments of a glucose sensor, the enzyme domain includes glucose oxidase (GOX); however other enzymes, for example, alcohol dehydrogenase, galactose oxidase or uricase oxidase, can also be used. In some embodiments, the enzyme domain is configured and arranged for detection of at least one of substance such as albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, various minerals, various metabolites, and the like. In a further embodiment, the sensor is configured and arranged to detect two or more of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, various minerals, various metabolites, and the like.

For an enzyme-based electrochemical glucose sensor to perform well, the sensor's response may be limited by neither enzyme activity nor co-reactant concentration. Because enzymes, including glucose oxidase, are subject to deactivation as a function of time even in ambient conditions, this behavior can be compensated for in forming the enzyme domain. In some embodiments, the enzyme domain is constructed of aqueous dispersions of colloidal polyurethane polymers including the enzyme. However, in alternative embodiments the enzyme domain is constructed from an oxygen enhancing material, such as silicone, or fluorocarbon, for example, in order to provide a supply of excess oxygen during transient ischemia. In some embodiments, the enzyme is immobilized within the domain. See, e.g., U.S. Patent Application Publication No. US-2005-0054909-A1.

In some embodiments, the enzyme domain is deposited onto the interference domain for a domain thickness of from about 0.05 micron or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 2, 2.5 or 3 microns to about 3.5, 4, 4.5, or 5 microns. However in some embodiments, the enzyme domain is deposited directly onto the electroactive surfaces. In other embodiments, the enzyme domain is formed by dip coating or spray coating one or more layers at a predetermined concentration of the coating solution, insertion rate, dwell time, withdrawal rate, or desired thickness.

In some embodiments, the sensor system comprises a plurality of sensor elements, each with different enzyme domain properties. As described elsewhere herein, in certain embodiments, the sensor system comprises a plurality of sensor elements each designed to have a different sensitivity or current sensitivity than the other sensor element(s). In one embodiment, the differences in sensor sensitivity or current density may be achieved by modifying each sensor element to have a different amount of enzyme. In other embodiments, one of the plurality of sensor elements may have an enzyme domain which comprises polymers that contain mediators and enzymes that chemically attach to the polymers. The mediator used may oxidize at lower potentials than hydrogen peroxide, and thus fewer oxidizable interferents are oxidized at these low potentials. Accordingly, one of the sensor elements may have a very low baseline (i.e., a baseline that approaches a zero baseline and that does not receive substantial signal contribution from non-glucose-related noise), such that the signal generated therefrom can be used to compare with the signal from another sensor element operating at a higher bias potential. By comparing the signals, the presence of interferents can be detected. Furthermore, in certain embodiments, the baseline present in the signal from the sensor element operating at a higher bias potential may be calculated (from the signal generated from the sensor element operating with a baseline of about zero) by comparing the signals from the two sensor elements (e.g., by subtracting one signal from another signal after accounting for scaling). In turn, signal contribution from non-glucose-related noise can be subtracted from the signal of the sensor element operating at a higher bias potential, thereby improving its signal's the signal to noise ratio, which results in greatly improved sensor accuracy. In certain embodiments, one of the plurality of sensor elements may have an enzyme domain which uses a mediator that may reduce or eliminate the need for oxygen, as the mediator take the place of oxygen in the enzyme reaction. Such a sensor element may be tuned for (and configured to detect) low oxygen environments, while other sensor elements are used in normal or high in vivo oxygen environments.

In some embodiments, the membrane system is provided with a diffusion resistance domain, also referred to as a diffusion resistance layer, a resistance domain, or a resistance layer. In some embodiments, the membrane system is situated more distal to the electrode relative to the enzyme, electrode, and interference domains. The diffusion resistance domain serves to control the flux of oxygen and other analytes (for example, glucose) to the underlying enzyme domain. As described in more detail elsewhere herein, there typically exists a molar excess of glucose relative to the amount of oxygen in blood, i.e., for every free oxygen molecule in extracellular fluid, there are typically more than 100 glucose molecules present (see, e.g., Updike et al., *Diabetes Care* 5:207-21 (1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels may be obtained only up to about 40 mg/dL. However, in a clinical setting, a linear response to glucose levels is desirable up to at least about 500 mg/dL.

The diffusion resistance domain of certain embodiments includes a semipermeable membrane that controls the flux of oxygen and glucose to the underlying enzyme domain, thereby rendering oxygen in non-rate-limiting excess. As a result, the upper limit of linearity of glucose measurement is extended to a much higher value than that which is achieved without the diffusion resistance domain. In some embodiments, the diffusion resistance domain exhibits an oxygen-to-glucose permeability ratio of approximately 200:1, but in other embodiments the oxygen-to-glucose permeability ratio is approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion may provide sufficient excess oxygen at all reasonable glucose and oxygen concentrations found in the subcutaneous matrix (See Rhodes et al., *Anal. Chem.*, 66:1520-1529 (1994)). In some embodiments, a lower ratio of oxygen-to-glucose is sufficient to provide excess oxygen by using a high oxygen soluble domain (for example, a silicone material) to enhance the supply/transport of oxygen to the enzyme membrane or electroactive surfaces. By enhancing the oxygen supply through the use of a silicone composition, for example, glucose concentration is less of a limiting factor. In other words, if more oxygen is supplied to the enzyme or electroactive surfaces, then more glucose can also be supplied to the enzyme without creating an oxygen rate-limiting excess. Although the description provided herein is directed to a resistance domain for a glucose sensor, the resistance domain can be modified for other analytes and co-reactants as well.

In one embodiment, the resistance domain includes a polyurethane membrane with both hydrophilic and hydrophobic regions to control the diffusion of glucose and oxygen to an analyte sensor, the membrane being fabricated from commercially available materials. Suitable hydrophobic polymer components include polyurethane and polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Diisocyanates that may be used include, but are not limited to, aliphatic diisocyanates containing from about 4 to about 8 methylene units. Diisocyanates containing cycloaliphatic moieties can also be useful in the preparation of the polymer and copolymer components of the membranes, in accordance with some embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials that can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

A suitable hydrophilic polymer component as employed in certain embodiments is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In other embodiments, a lower ratio of oxygen-to-glucose is sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Application Publication No. US-2005-0090607-A1.

In yet other embodiments, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

In some embodiments, the resistance domain deposited onto the enzyme domain yields a domain thickness of from about 0.05 microns or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 2, 2.5 or 3 microns to about 3.5, 4, 4.5, or 5 microns. The resistance domain can be deposited onto the enzyme domain using any of a variety of known deposition techniques, such as, but not limited to, vapor deposition, spray coating, or dip coating. In some embodiments, spray coating is desired. The spraying process atomizes and mists the solution, and therefore most or all of the solvent is evaporated prior to the coating material settling on the underlying domain, thereby minimizing contact of the solvent with the enzyme.

In some embodiments, the sensor system comprises a plurality of sensor elements, each with different diffusion resistance domain properties, such that each sensor element is configured to control the flux of the analyte or a co-analyte differently than the other sensor elements. For example, in some of these embodiments, each or some of the diffusion resistance domains of certain sensor element(s) can have sensitivities or current densities different from the other sensor elements, which allows for accuracy to be tuned or designed at low and high values, for example. Differences in diffusion resistance domain properties can be achieved by modifying the diffusion resistance domain, e.g., by modifying the thickness or composition of the diffusion resistance domain.

In some sensors, membranes are configured to provide, to generate, or to consume hydrogen peroxide molecules, depending upon the relevant physiological range that the sensor is configured to measure. This arrangement, in turn provides for more accurate measurements. Membranes configured to consume hydrogen peroxide molecules include superoxide dismutase, catalase, horseradish, and/or like compounds.

In one embodiment including first and second sensor elements with first and second membranes, respectively, the first and second membranes each comprise an enzyme (e.g., glucose oxidase) configured to generate hydrogen peroxide by reaction of glucose and oxygen with the enzyme, wherein the first and second sensor elements each comprise an electrode configured to measure at least some of the hydrogen peroxide generated within the first and second membranes. In certain of these embodiments, the first membrane is configured to consume more hydrogen peroxide than the second membrane system, for example, by providing in one of the membranes a hydrogen peroxide-consuming enzyme configured to reduce exogenous hydrogen peroxide originating from a source outside the sensor. Although one method or system for consuming hydrogen peroxide is described herein, any of a variety of systems and methods for consuming hydrogen peroxide in a membrane can alternatively or additionally be used. Advantageously, by configuring one membrane to consume more hydrogen peroxide than another membrane, the glucose-related to non-glucose-related signal ratio of one of the sensors element or its sensor sensitivity or current density can be adjusted (e.g., relative to the other sensor element). In certain embodiments, one of the membranes is configured to direct more hydrogen peroxide to its associated electrode than the other membrane, which can be accomplished by a membrane configured to block at least some of the hydrogen peroxide from escaping from the sensor element, for example. Although one method of directing hydrogen peroxide is described herein, any of a variety of systems and methods for directing hydrogen peroxide in a membrane can alternatively or additionally be used. Advantageously, by designing one membrane to direct more hydrogen peroxide to its associated electrode than the other membrane, the glucose-related to non-glucose-related signal ratio of one of the sensor element or its sensor sensitivity or current density can be adjusted (e.g., relative to the other sensor element).

In some embodiments, sensor elements comprising the membrane system have been found to provide sustained function (at least 90% signal strength), even at low oxygen levels (for example, at about 0.6 mg/L $O_2$). While not wishing to be bound by theory, it is believed that the diffusion resistance domain provides sufficient diffusion resistivity, such that oxygen limitations of the sensor occur at a substantially lower oxygen concentration than with conventional sensors.

In some embodiments, one or more of the sensor elements of a sensor system exhibits a 100±10% functionality, or about 100% functionality over physiological glucose concentrations (from about 40 mg/dL to about 400 mg/dL) at oxygen concentrations as low as about 0.6 mg/L or less, or about 0.3 mg/L or less, or about 0.25 mg/L or less, or about 0.15 mg/L or less, or about 0.1 mg/L or less, or about 0.05 mg/L or less. The glucose sensors of some embodiments consume 1 µg or less of enzyme over their operational lifetimes (e.g., 7 days or less).

Many conventional analyte sensors encounter initial noise caused in part by metabolic processes that react due to a foreign body response when a sensor is introduced into the body. It has been found that with conventional analyte sensors inserted into a host, measurement performance is generally better a few days post-insertion, as compared to measurement performance during the time period right after insertion. This effect is evident by the increased level of non-analyte-related signals or the suppression of analyte-related signals which occurs during approximately the first 2 to 36 or more hours after sensor insertion. These measurement anomalies are typically resolved spontaneously, after which the sensors become less noisy, show improved sensitivity, and are generally more accurate than during the period right after insertion. Moreover, with these conventional analyte sensors, during the period right after insertion, non-analyte-related signals often predominate over analyte signals when hosts are sleeping or sedentary for a period of time. Other examples of noise are described in more detail in U.S. Pat. No. 7,310,544. It is contemplated that the sensors described herein of certain embodiments can include a biointerface membrane that encases the entire sensor or encases a portion of the sensor, to minimize migration or growth of host inflammatory cells, immune cells, or soluble factors to sensitive regions of the device. In some embodiments, the biointerface membrane promotes vascularization of the device and facilitates transport of solutes across the device-tissue interface to enhance the device's performance. In some embodiments, a sensor with a biointerface domain has an initial sleep period (e.g., the first few hours, days, or weeks after implant), during which the sensor does not provide accurate measurements, as vascularization of the sensor progresses. Other embodiments of the biointerface are described in more detail in U.S. Patent Application Publication No. US-2007-0027370-A1.

In some embodiments of the sensor system comprising a first sensor element with a first biointerface domain and a second sensor element with a second biointerface domain, the first and second biointerface membranes comprise three dimensional architectures that are different from each other. For example, the three dimensional architecture of the first biointerface membrane can comprise pores defined by a first range of sizes, and the three dimensional architecture of the second biointerface membranes can comprise pores defined by a second range of sizes. In some exemplary embodiments, the first range of sizes (e.g., less than about 20 microns) is smaller than the second range of sizes (e.g., greater than about 20 microns). As another example, the three dimensional architecture of the first or second sensor element is porous while that of the other sensor element is nonporous. Other embodiments of the three dimensional architecture are described in more detail in U.S. Patent Application Publication No. US-2005-0251083-A1.

Figure 3:
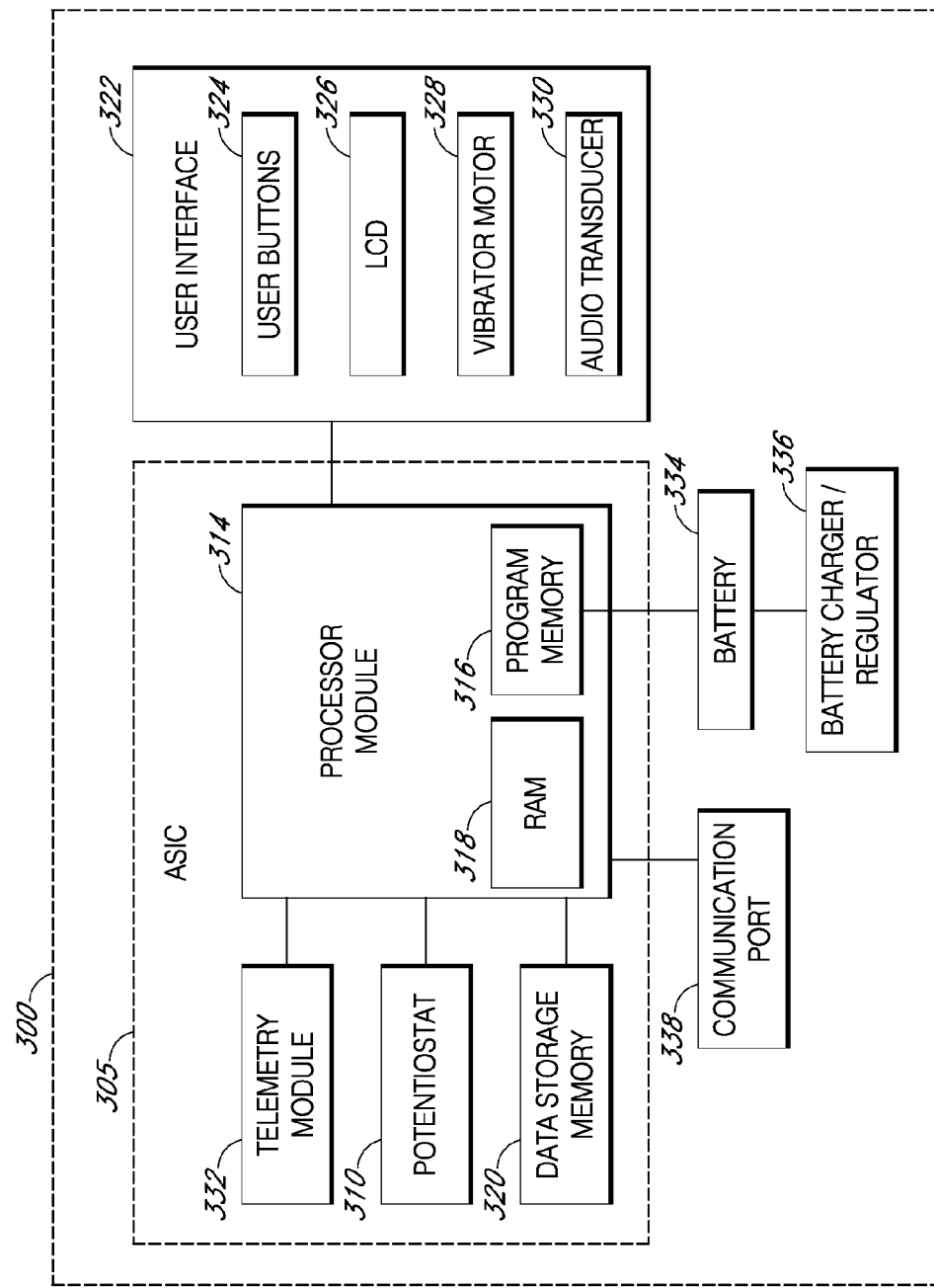
FIG. 3 is a block diagram illustrating continuous glucose sensor electronics, in one embodiment.

FIG. 3 is a block diagram illustrating one embodiment of the sensor electronics 300. In this embodiment, the ASIC 305 is coupled to a communication port 338 and a battery 334. Although the illustrated embodiment includes an Application Specific Integrated Circuit (ASIC) 305 that includes much of the electronic circuitry, in other embodiments, the ASIC 305 is replaced with one or more of any suitable logic device, such as, for example, field programmable gate arrays (FPGA), microprocessors, analog circuitry, or other digital or analog circuitry.

In the embodiment shown in FIG. 3, a potentiostat 310 is coupled to a glucose sensor in order to receive sensor data from the glucose sensor. Any of a variety of mechanisms can be used to couple the potentiostat 310 to the glucose sensor. For example, in one embodiment, the one or more ends of the working electrode(s) is exposed to provide electrical connection between the potentiostat and the first and second sensor elements. In one embodiment, the potentiostat 310 provides a voltage to the glucose sensor in order to bias the sensor to enable measurement of a current value indicative of the analyte concentration in the host (also referred to as the analog portion). The potentiostat can have one channel or multiple channels, depending on the number of working electrodes, for example. In some embodiments, the potentiostat 310 includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 310.

A processor module 314 is the central control unit that controls the processing of the sensor electronics. In some embodiments, the processor module 314 is formed as part of a custom chip, such as an ASIC, however a computer system other than an ASIC can be used to process data as described herein, for example a microprocessor can be used for some or all of the sensor electronics module processing. The processor module 314 typically provides a program memory 316, which provides semi-permanent storage of data, for example, storing data such as sensor identifier (ID) and programming to process data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 318 can be used for the system's cache memory, for example for temporarily storing recent sensor data.

In some embodiments, the processor module 314 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, such as when the potentiostat 310 is configured to measure the analyte at discrete time intervals, these time intervals determine the sample rate of the digital filter. In some alternative embodiments, wherein the potentiostat 310 is configured to continuously measure the analyte, for example, using a current-to-frequency converter, the processor module 314 can be programmed to request a digital value from the integrator at a predetermined time interval, also referred to as the acquisition time. In these alternative embodiments, the values obtained by the processor module 314 are advantageously averaged over the acquisition time due the continuity of the current measurement. Accordingly, the acquisition time determines the sample rate of the digital filter.

In one embodiment, the processor module 314 is further configured to generate data packages for transmission to one or more display devices. Furthermore, the processor module 314 generates data packets for transmission to these outside sources, e.g., via telemetry. As discussed above, the data packages can be customizable for each display device, for example, and may include any available data, such as displayable sensor information having customized sensor data or transformed sensor data, sensor/sensor electronics module ID code, raw data, filtered data, calibrated data, rate of change information, trend information, error detection or correction, or the like. A data storage memory 320 is operably connected to the processor module 314 and is configured to store a variety of sensor information. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory 220 stores sensor information such as raw sensor data (one or more raw analyte concentration values), transformed sensor data, or any other displayable sensor information.

In some embodiments, the sensor electronics are configured to receive and store contact information in the data storage memory (or program memory), including a phone number or email address for the sensor's host or health care providers for the host (e.g., family member(s), nurse(s), doctor(s), or other health care provider(s)), which enables communication with a contact person (e.g., via phone, pager or text messaging in response to an alarm (e.g., a hypoglycemic alarm that has not been responded to by the host)). In some embodiments, user parameters can be programmed into (or modified in) the data storage memory (or program memory) of the sensor electronics module, via a display device such as a personal computer, personal digital assistant, or the like. User parameters can include contact information, alert/alarms settings (e.g., thresholds, sounds, volume, or the like), calibration information, font size, display preferences, defaults (e.g., screens), or the like. Alternatively, the sensor electronics module can be configured for direct programming of certain user parameters.

In one embodiment, clinical data of a medical practitioner is uploaded to the sensor electronics and stored on the data storage memory 320, for example. Thus, information regarding the host's condition, treatments, medications, etc., can be stored on the sensor electronics and can be viewable by the host or other authorized user. In one embodiment, certain of the clinical data are included in a data package that is transmitted to a display device in response to triggering of an alert. The clinical data can be uploaded to the sensor electronics via any available communication protocol, such as direct transmission via a wireless Bluetooth, infrared, or RF connection, or via a wired USB connection, for example. Additionally, the clinical data can be uploaded to the sensor electronics via indirect transmission, such as via one or more networks (e.g., local area, personal area, or wide area networks, or the Internet) or via a repeater device that receives the clinical data from a device of the medical practitioner and retransmits the clinical data to the sensor electronics module.

Any of a variety of configurations of separate data storage and program memories can be used, including one or multiple memories that provide the necessary storage space to support the sensor electronic data processing and storage requirements. Accordingly, the described location of storage of any particular information or programming is not meant to be limiting, but rather exemplary.

In some embodiments, the sensor electronics is configured to perform smoothing or filtering algorithms on the sensor data (e.g., raw data stream or other sensor information), wherein the smoothed or filtered data is stored in the data storage memory as transformed data. U.S. Patent Application Publication No. US-2005-0043598-A1, U.S. Patent Application Publication No. US-2007-0032706-A1, U.S. Patent Application Publication No. US-2007-0016381-A1 and U.S. Patent Application Publication No. US-2008-0033254-A1 describe some algorithms useful in performing data smoothing or filtering herein (including signal artifacts replacement).

In some embodiments, the sensor electronics are configured to calibrate the sensor data, and the data storage memory 320 stores the calibrated sensor data points as transformed sensor data. In some further embodiments, the sensor electronics are configured to wirelessly receive calibration information from a display device, from which the sensor electronics module is configured to calibrate the sensor data. U.S. Pat. Nos. 7,310,544 and 6,931,327 describe some algorithms useful in sensor calibration herein.

In some embodiments, the sensor electronics are configured to perform additional algorithmic processing on the sensor data (e.g., raw data stream or other sensor information) and the data storage memory 320 is configured to store the transformed sensor data or sensor diagnostic information associated with the algorithms. U.S. Pat. Nos. 7,310,544 and 6,931,327 describe some algorithms that can be processed by the sensor electronics module.

A user interface 322 can include any of a variety of interfaces, such as one or more buttons 324, a liquid crystal display (LCD) 326, a vibrator 328, an audio transducer (e.g., speaker) 330, backlight, or the like. A backlight can be provided, for example, to aid the user in reading the LCD in low light conditions. The components that comprise the user interface 322 provide controls to interact with the user (e.g., the host). One or more buttons 324 can allow, for example, toggle, menu selection, option selection, status selection, yes/no response to on-screen questions, a "turn off" function (e.g., for an alarm), a "snooze" function (e.g., for an alarm), a reset, or the like. The LCD 326 can be provided, for example, to provide the user with visual data output. The audio transducer 330 (e.g., speaker) provides audible signals in response to triggering of certain alerts, such as present or predicted hyper- and hypoglycemic conditions. In some embodiments, audible signals are differentiated by tone, volume, duty cycle, pattern, duration, or the like. In some embodiments, the audible signal is configured to be silenced (e.g., snoozed or turned off) by pressing one or more buttons 324 on the sensor electronics module or by signaling the sensor electronics module using a button or selection on a display device (e.g., key fob, cell phone, or the like).

In some embodiments, the audio transducer 330 is mounted to the circuit board or the sensor electronics module housing. In some embodiments, the sound produced by the audio transducer 330 exits the device from a sound port in the sensor electronics, such as a hole on the sensor electronics. The hole may be waterproofed or otherwise protected from moisture by a waterproof material that easily allows sound waves there through. In one embodiment, the hole is protected from moisture by an acoustically transparent venting material (wherein the material allows at least about 60%, 70%, 80%, 90%, 95%, or more of the transmitted sound waves therethrough), such as a screw-in vent, a press-fit vent, a snap-in vent, an o-ring vent, and adhesive vent, or the like. One manufacturer that provides acoustically transparent venting material is W.L. Gore & Associates (Elkton, Md.) under the trade name Protective Vents (Acoustic Vents).

The vibrator 328 can include a motor that provides, for example, tactile signals or alerts for reasons such as described with reference to the audio transducer, above. In one embodiment, the vibrator motor 328 provides a signal in response to triggering of one or more alerts, which can be triggered by the processor module 314 that processes algorithms useful in determining whether alert conditions associated with one or more alerts have been met, for example, present or predicted hyper- and hypoglycemic conditions. In some embodiments, one or more different alerts are differentiated by intensity, quantity, pattern, duration, or the like. In some embodiments, the alarm is configured to be silenced (e.g., snoozed or turned off) by pressing one or more buttons 324 on the sensor electronics or by signaling the sensor electronics using a button or selection on a display device (e.g., key fob, cell phone, or the like).

In some embodiments, the vibrator motor 328 is mounted to the circuit board or the sensor electronics housing. The diameter of the motor may be less than or equal to about 6 mm, 5 mm, 4 mm, 3.5 mm, 3 mm, 2.5 mm, or 2 mm. The overall length of the vibrator motor may be less than or equal to about 18 mm, 16 mm, 14 mm, 12 mm, or 10 mm. By providing a low power vibrator motor, the motor can be placed in the sensor electronics without significantly affecting the low profile nature of the on-skin sensor electronics.

In some embodiments, the vibrator motor 328 is used to provide a vibratory alarm that creates vibration or movement of the sensor within the host. While not wishing to be bound by theory, it is believed that a concentration increase of non-analyte-signal-causing electroactive species, such as electroactive metabolites from cellular metabolism and wound healing, can interfere with sensor function and cause noise observed during host start-up or sedentary periods. For example, local lymph pooling, which can occur when a part of the body is compressed or when the body is inactive, can cause, in part, this local build up of interferents (e.g., electroactive metabolites). Similarly, a local accumulation of wound healing metabolic products (e.g., at the site of sensor insertion) likely causes noise on the sensor during the first few hours to days after sensor insertion. Accordingly, it is believed vibration or movement of the sensor at the insertion site, after sensor insertion, can reduce or eliminate pooling of local interfering species caused by the wound healing process described above. In some embodiments, the sensor is vibrated or moved at predetermined intervals or in response to noise artifacts detected on the sensor signal. U.S. Patent Application Publication No. US-2005-0043598-A1, U.S. Patent Application Publication No. US-2007-0032706-A1, U.S. Patent Application Publication No. US-2007-0016381-A1 and U.S. Patent Application Publication No. US-2008-0033254-A1 describe systems and methods for detection of noise artifacts, noise episodes or classification of noise, which can be useful with the embodiments described herein.

In another alternative embodiment, the sensor electronics are configured to transmit sound waves into the host's body (e.g., abdomen or other body part) that are felt by the host, thereby alerting the host without calling attention to the host, or allowing a hearing-impaired visually-impaired, or tactilely-impaired host to be alerted. In some embodiments, the sound waves are transmitted into the host's body using the electrodes of the sensor itself. In some embodiments, one or more transcutaneous electrodes (other than the electrodes related to analyte measurement) are provided for transmitting sound waves. In some embodiments, electrodes are provided in the adhesive patch that holds the sensor/sensor electronics module onto the host's body, which can be used to transmit the sound waves. In some embodiments, different sound waves are used to transmit different alarm conditions to the host. The sound waves can be differentiated by any sound characteristic, such as but not limited to amplitude, frequency and pattern.

In another alternative embodiment, mild electric shock can be used to transmit one or more alarms to the host. The level of shock can be designed such that the shock is not overly uncomfortable to the host; however, the intensity of the level of shock can be configured to increase when a host does not respond to (e.g., snooze or turn off) an alert within an amount of time. In some embodiments, the shock is delivered to the host's body using the electrodes of the sensor itself. In some embodiments, the sensor system includes one or more additional electrodes configured for delivering the shock to the host (alone or in combination with the electrodes related to analyte measurement). In still another example, the one or more electrodes are disposed on the host's skin, such as in the adhesive patch, for delivering the shock. Alternatively, one or more additional patches, each including an electrode, are provided, for delivering the shock. The additional patches can be in wired or wireless communication with the sensor electronics module.

A telemetry module 332 is operably connected to the processor module 314 and provides the hardware, firmware, and/or software that enable wireless communication between the sensor electronics and one or more display devices. A variety of wireless communication technologies that can be implemented in the telemetry module 332 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, or the like. In one embodiment, the telemetry module comprises a Bluetooth chip. In some embodiments, Bluetooth technology is implemented in a combination of the telemetry module 332 and the processor module 314.

A battery 334 is operatively connected to the processor module 314 (and possibly other components of the sensor electronics) and provides the necessary power for the sensor electronics. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries is used to power the system. In still other embodiments, the receiver is transcutaneously powered via an inductive coupling, for example.

A battery charger or regulator 336 can be configured to receive energy from an internal or external charger. In one embodiment, a battery regulator (or balancer) 336 regulates the recharging process by bleeding off excess charge current to allow all cells or batteries in the sensor electronics module to be fully charged without overcharging other cells or batteries. In some embodiments, the battery 334 (or batteries) is configured to be charged via an inductive or wireless charging pad. Any of a variety of known methods of charging batteries can be employed, which can be implemented with the system described herein, including wired (cable/plug) and wireless methods.

One or more communication ports 338, also referred to as external connector(s), can be provided to allow communication with other devices, for example a PC communication (com) port can be provided to enable communication with systems that are separate from, or integral with, the sensor electronics module. The communication port, for example, can comprise a serial (e.g., universal serial bus or "USB") communication port, allows for communicating with another computer system (e.g., PC, personal digital assistant or "PDA," server, or the like). In one exemplary embodiment, the sensor electronics is able to transmit historical data to a PC or other computing device for retrospective analysis by a patient or physician.

In continuous analyte sensor systems, the processor module of the sensor electronics and/or another computer system is configured to execute prospective algorithms used to generate transformed sensor data or displayable sensor information, including, for example, algorithms that: evaluate a clinical acceptability of reference or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor or sensor data, detect signal artifacts (noise), replace signal artifacts, determine a rate of change or trend of the sensor data, perform dynamic and intelligent analyte value estimation, perform diagnostics on the sensor or sensor data, set modes of operation, evaluate the data for aberrancies, or the like, which are described in more detail in U.S. Pat. Nos. 7,310,544, 6,931,327, U.S. Patent Application Publication No. US-2005-0043598-A1, U.S. Patent Application Publication No. US-2007-0032706-A1, U.S. Patent Application Publication No. US-2007-0016381-A1, U.S. Patent Application Publication No. US-2008-0033254-A1, U.S. Patent Application Publication No. US-2005-0203360-A1, U.S. Patent Application Publication No. US-2005-0154271-A1, U.S. Patent Application Publication No. US-2005-0192557-A1, U.S. Patent Application Publication No. US-2006-0222566-A1, U.S. Patent Application Publication No. US-2007-0203966-A1 and U.S. Patent Application Publication No. US-2007-0208245-A1. Furthermore, the sensor electronics can be configured to store the transformed sensor data (e.g., values, trend information) and to communicate the displayable sensor information to a plurality of different display devices. In some embodiments, the display devices are "dummy" devices, namely, they are configured to display the displayable sensor information as received from the sensor electronics, without any additional sensor data processing.

In an exemplary embodiment of an electrochemical analyte sensor, the sensor electronics is operatively connected to at least one sensor element configured to measure an analyte concentration in a first predetermined range and a second sensor element configured to measure an analyte concentration in a second predetermined range. In the example, the first range is for the most part different from the second range. In the exemplary embodiment, there can be an overlap of values in both ranges. For example, the first range can be used to measures glucose concentration values from about 0 mg/dL to about 100 mg/dL and the second range can be used to measure glucose concentration values from about 80 mg/dL to about 400 mg/dL.

A variety of conventional continuous glucose sensors have been developed for detecting and quantifying glucose concentration in a host. These sensors typically require one or more blood glucose measurements, or the like, from which calibration of the continuous glucose sensor is performed to calculate the relationship between the current output of the sensor and blood glucose measurements, so that meaningful glucose concentration values can be accurately calculated and communicated to a patient or doctor. Unfortunately, continuous glucose sensors can be sensitive to changes in the baseline current or sensitivity over time, for example, due to changes in a host's metabolism, maturation of the tissue at the biointerface of the sensor, presence of interfering species which cause a measurable increase or decrease in the signal, or the like. Therefore, in addition to initial calibration, continuous glucose sensors may be responsive to baseline or sensitivity changes over time. To achieve this, recalibration of the sensor may be required periodically. Consequently, users of conventional continuous glucose sensors may be required to obtain numerous blood glucose measurements daily or weekly, in order to maintain accurate calibration of the sensor over time. Some of the embodiments provide improved calibration techniques that utilize calibration and matched data points of one sensor element to further calibrate the second sensor element. In certain embodiments, a known reference value can be used to calibrate a plurality of sensor elements accurately.

Figure 4:
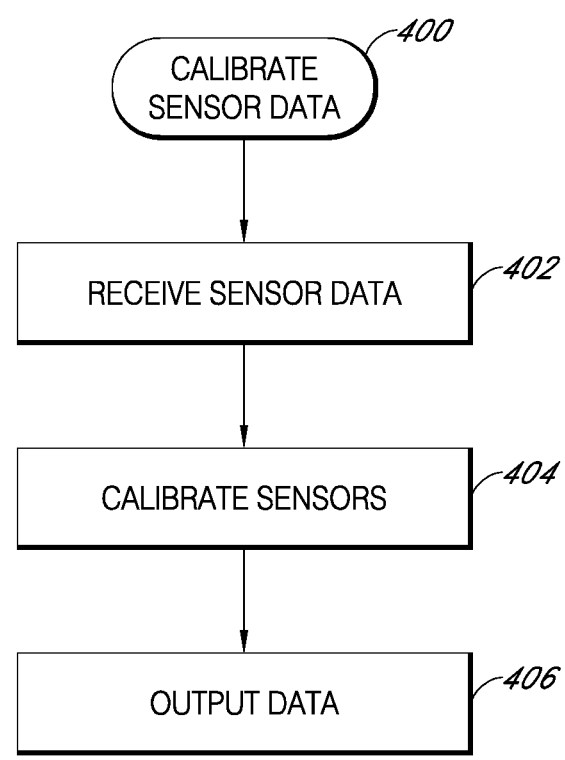
FIG. 4 is a flowchart illustrating the measuring and processing of sensor data, in one embodiment.

FIG. 4 is a flowchart 400 illustrating calibration and output of sensor data, in one embodiment. Some of the embodiments provide a method for processing data from a sensor system configured for measurement of an analyte concentration in a host, where the sensor system includes a plurality of sensor elements, each or some of which measure different ranges of analyte concentration within the host and/or different time periods of implantation with a predetermined level of accuracy.

In step 402, the processor module receives sensor data (e.g., a data stream), including one or more time-spaced sensor data points, from one or more of the plurality of sensor elements, each or some of which can be in wired or wireless communication with the sensor. In some embodiments, wherein the sensor system has two or more sensors elements configured and arranged to provide values in different analyte concentration ranges, the sensor data from the two or more sensor elements is received substantially simultaneously, such as within the same or serially received data transmissions. In some embodiments, wherein the sensor system has two or more sensor elements configured and arranged to provide values for different periods of implantation, sensor data from each of the sensor elements is received serially, for example.

In step 404, the processor module calibrates the first and/or second sensor elements. In some embodiments, calibrating the first sensor element includes processing an external reference value and/or one or more values provided by a manufacturer. For example, the user can administer a self-monitored blood analyte test to obtain an analyte value (e.g., a point) using any suitable analyte sensor, and then enter the numeric analyte value into the computer system.

In some embodiments, when the received sensor data is within an overlapping range of the predetermined measurement range of two sensor elements, the two sensor elements can be calibrated with the same calibration information. In some of these embodiments, a first sensor element is calibrated first, and then one or more calibrated sensor values from the first sensor element are then used to calibrate a second and/or another sensor element.

In some embodiments, a known relationship is defined between the first and second sensor elements, for example a relationship between the sensitivities or current densities of the first and second sensor elements, which is determined from prior in vitro and/or in vivo data. In such an embodiment, after calibration of the first sensor element, the known relationship, which is defined by a function, is then used to calibrate the second sensor element. In some embodiments, wherein first and second sensor elements are used for different time periods of a sensor session and/or sensor implantation, sensor data from one sensor element is used to calibrate the other sensor element during an overlapping time period of use.

In step 406, an output module provides output to the user via the user interface, for example. The output is associated with one or more measured analyte values, which are determined by converting the received sensor data into calibrated sensor data. User output can be in the form of a numeric estimated analyte value, an indication of directional trend of analyte concentration, and/or a graphical representation of the estimated analyte data over a period of time, for example. Other representations of the estimated analyte values, such as audio or tactile representations, for example, are also possible.

In some embodiments, wherein a plurality of sensor elements are configured and arranged to accurately measure within certain predetermined analyte concentration ranges, the processor module or output module is configured to output data, by using calibrated sensor data obtained from the particular sensor element associated with the range within which the measurement falls within. In some embodiments, wherein a plurality of sensor elements are configured and arranged for different time periods of sensor function, sensor data from one sensor element, including one or more calibrated sensor values, can be used to calibrate another sensor element, and so forth.

As discussed in more detail elsewhere herein, some analyte sensors can have an initial instability time period during which it is unstable for environmental, physiological, or other reasons. For example, for a sensor element implanted subcutaneously, its stabilization can be dependent upon the maturity of the tissue ingrowth around and within the sensor element (see, e.g., U.S. Patent Application Publication No. US-2005-0112169-A1). Accordingly, determination of sensor stability may involve waiting a first time period. As examples, wholly implantable sensors typically require a time period to allow for sufficient tissue ingrowth, and transdermal (e.g., transcutaneous) sensors are believed to typically have an initial period of noise due in part to wound healing within the host's tissue. Depending on the specific configuration of the sensor, the waiting period may last from about one minute to about three weeks. The waiting period can be determined by pretesting the sensor under similar conditions, or by analysis of the sensor data establishing that the sensor is stable. In some embodiments of a sensor system comprising a first sensor element and a second sensor element, the second sensor element is configured to measure the analyte concentration and provide data during the first time period. Once the first sensor element is deemed stable, data from the first sensor element may still require calibration, in order for it to provide accurate values. In some embodiments, in which sensor data from the second sensor element exhibits a correlative or predictive relationship with sensor data from the first sensor element, data from the second sensor element can be used to calibrate data from the first sensor element. Calibration of sensor data from the first sensor element using sensor data provided by the second sensor element can facilitate the use of the first sensor element data sooner and may reduce or even obviate the need to calibrate the first sensor element with single point calibration techniques, e.g., fingerstick tests, optical measuring techniques, etc.

As described above, in some embodiments, the sensor system comprises a plurality of sensor elements, each configured to measure values in various ranges. As also described above, although each sensor element of the sensor system can be "tuned" to a particular range, this arrangement does not preclude each sensor element from measuring analyte values across a physiologically relevant range, and thereby providing valuable information. Accordingly, it is contemplated that in certain embodiments, error correction comprising error checking is used. For example, error checking can comprise checking for data integrity by comparing sensor data from two or more sensor elements.

Figure 5:
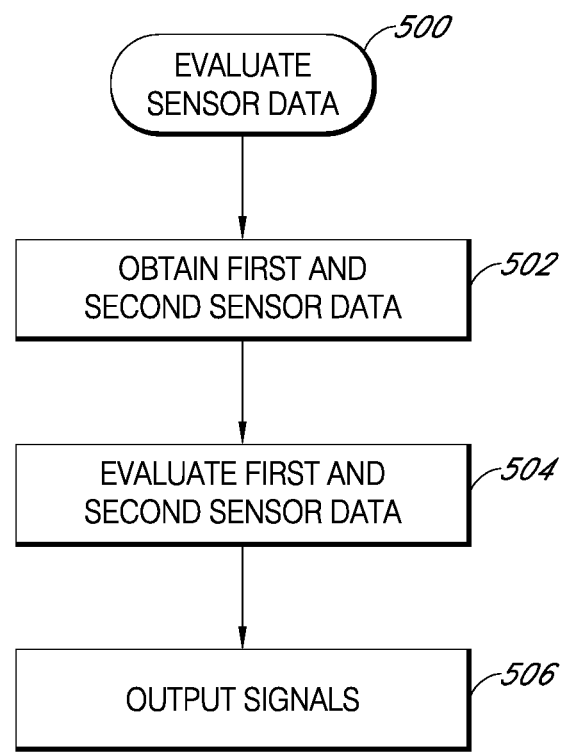
FIG. 5 is a flowchart illustrating the measuring and processing of sensor data, in another embodiment.

FIG. 5 is a flowchart 500 that illustrates measuring and processing of sensor data, in one embodiment. In step 502, the processor module receives sensor data (e.g., a data stream) including one or more time-spaced sensor data points, from one or more of the plurality of sensor elements, which can be in wired or wireless communication with the sensor, such as described in more detail elsewhere herein. In step 504, the processor module is configured to evaluate sensor data from one or more of the plurality of sensor elements. In some embodiments, the processor module evaluates the sensor data by polling sensor data from the one or more of the plurality of sensor elements. It is contemplated that a wide range of polling intervals are possible, which can be chosen with consideration of processing power and accuracy. For example, polling can occur about every 1 second, 10 seconds, 1 minute, 5 minutes, or any other interval suitable for the application contemplated.

In some embodiments, the processor module compares sensor data from a plurality of sensor elements. For example, the amplitudes of a first sensor element data (i.e., sensor data from a first sensor element) is compared to amplitudes of a second sensor element data (i.e., sensor data from a second sensor element). Accordingly, the sensor system can provide highly accurate measurement of analyte concentration by comparing the plurality of sensor element measurements.

In some embodiments, the processor module averages and/or integrates the sensor data from a plurality of sensor elements. The processor module may also accord the data generated by each of the plurality of sensor elements with a different weight. A weighted arithmetic average can be used to estimate analyte concentration and be calculated by the equation:

$$\bar{x} = \frac{\sum_{i=1}^{n} w_i x_i}{w_i}$$

in which $x_i$ is the analyte concentration measurement from a particular sensor element, $\bar{x}$ is the mean analyte concentration to be estimated, n is the number of sensor elements, and $w_i$ is the weight accorded to the analyte concentration measurement from that particular sensor element. It is contemplated that other weighted means (e.g., a weighted geometric mean or a weighted harmonic mean) may also be used, in accordance with other embodiments. In other embodiments, a weighted sum is used. A weighted sum may be calculated by the equation:

$$\bar{x} = \sum_{i=1}^{n} w_i x_i$$

In an exemplary embodiment, the sensor system processes data by taking first sensor element data and second sensor element data and weighting both about equally to obtain values in the overlapping ranges of the first and second sensor elements. Other examples include taking data from one sensor element and weighting it more heavily than data from another sensor element (e.g., taking 80% of a first sensor element data and 20% of a second sensor element data to obtain values in the first data range).

In an exemplary embodiment, the sensor system comprises two sensor elements, with a first sensor element tuned to a glucose concentration of about 30 mg/dL to about 100 mg/dL and a second sensor element tuned to a glucose concentration of about 80 mg/dL to about 500 mg/dL. The first and second sensor elements generate first and second signals, respectively. During use, the first signal and the second signal may be averaged or integrated to generate an estimate of a glucose concentration value. In certain embodiments, the weights accorded to the first signal and the second signal may depend on an initial glucose concentration value estimation. For example, if the initial glucose concentration value was estimated to be about 35 mg/dL, the sensor electronics may be programmed to instruct the processor to accord more weight to the first sensor element, and less weight (or no weight) accorded to the second sensor element. Instead, if the initial glucose concentration value was estimated to be about 300 mg/dL, the processor may be instructed to accord more weigh the second sensor element, and less weight (or no weight) to the first sensor element.

It should be understood that the distribution of weights among the different sensor elements may be a function of a parameter other than an analyte glucose concentration value. For example, the distribution of weights may be a function of any parameter (e.g., a parameter that affects measurement accuracy) or plurality of variables including, but not limited to, initial analyte concentration measurement, body temperature, oxygen concentration in host, presence of interferents, time since initiation of the sensor session, and combinations thereof. Additionally, the weight distribution among the different sensor elements may be based at least in part on an estimated value of the parameter and the estimated value's proximity to the different ranges associated with the parameters. For example, in a sensor system comprising three sensors elements, with a first sensor element tuned to an oxygen concentration range of from about 0.1 mg/L to 0.3 mg/L, a second sensor element tuned to an oxygen concentration range of from about 0.3 mg/L to 0.4 mg/L, and third sensor element tuned to an oxygen concentration range of from about 0.4 mg/L to 0.6 mg/L, an oxygen concentration estimation of 0.5 mg/L may result in the processor module according most weight to the third sensor element, less (or no) weight to the second sensor element, and even less (or no) weight to the first sensor element.

In some embodiments, at least two of the plurality of sensor elements may be configured (e.g., by membrane design) to have substantially the same baseline, but with different sensor sensitivities. In these embodiments, subtraction of one signal from the other signal with the same baseline can result in an additional signal that is substantially free from noise contribution (e.g., from interferents), because the noise component is subtracted out. Having an extra signal can be advantageous as it provides another basis for comparison. Also, it can provide for improved polling of sensor data. In addition, because this extra signal includes substantially no noise contribution, it has a very high signal to noise ratio, and thus can provide high analyte concentration measurement accuracy.

In various embodiments, the data provided by one sensor element signal is used during intervals of time when another sensor element is unable to obtain accurate measurements. For example, if a first sensor element is unable to obtain accurate data, during an interval of 5 minutes due to noise or other causes, data values from a second sensor element are used to fill in values for that particular 5-minute interval. In some embodiments, the values calculated are based completely on the second sensor element, but in other embodiments, the values are calculated by weighting data from both sensor elements. The weight accorded to the second sensor element versus the first sensor element can be dependent on the accuracy of the two sensor elements. For example, if during a time period the first sensor element is determined to be much more accurate than the second sensor element, the weight percentage accorded to data provided by the first sensor element can be, e.g., about 0.9 and that of the second sensor element can be, e.g., about 0.1. However, if during a time period the first and second sensor elements are both providing data that are determined to be similarly accurate, both sensor elements can be accorded about equal weight percentages. This weight distribution mechanism of data from a plurality of different sensor elements can reduce noise, thereby providing smoother and more accurate data. Evaluations that can be provided by the processor module include, for example, error correction, supplementation of sensor data, weighting of various sensors' data, and the like. It is contemplated that a wide range of weighted averages are possible.

In some embodiments, the processor module is configured to evaluate sensor data from a plurality of sensor elements by evaluating an accuracy of the one or more sensor data using known statistical and/or clinical evaluation methods. In some embodiments, the processor module evaluates accuracy of sensor data by comparing different levels of accuracy (e.g., reference data points within the overlapping portion of the first and second ranges of first and second sensor elements). In some embodiments, evaluating accuracy includes evaluating noise (e.g., analyte-related to non-analyte-related signal ratios of sensor data from two or more sensor elements). In some embodiments, the processor module evaluates the sensor data in order to validate one or more of the plurality of sensor elements and/or associated sensor data.

In step 506, an output module provides output to the user via the user interface, for example. User output can be in the form of any of the variety of representations described elsewhere herein, such as the representations described in regard to step 406.

Figure 6A:
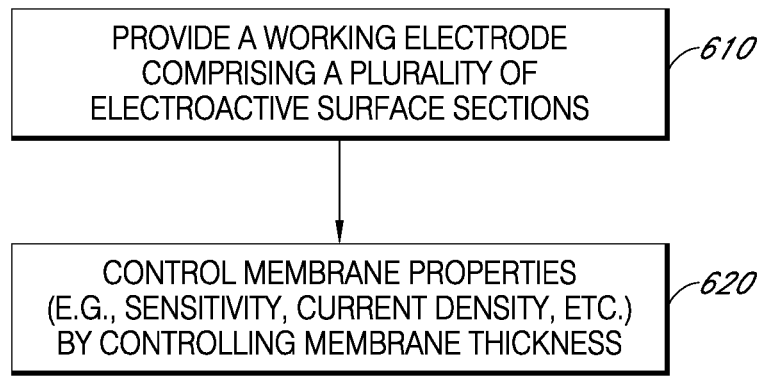
FIG. 6A is a flowchart illustrating one embodiment for manufacturing of a sensor system.

It is contemplated that the electrodes and sensor elements described herein can be manufactured by employing a variety of techniques, such as drop coating, spray coating, and dip coating, for example. FIG. 6A is a flowchart summarizing the steps of one embodiment for manufacturing a working electrode, such as the one illustrated in FIG. 1A, which comprises a plurality of sensor elements, each configured to measure analyte concentration in a range (e.g., analyte concentration range, time period range during a sensor session, etc.) different from that of the other sensor element(s). In step 610, a working electrode comprising a plurality of discrete electroactive surface sections is provided, with each section spaced apart from the other(s) along the longitudinal axis of the working electrode. In step 620, membranes are applied onto the plurality of electroactive surface sections by a dip coating process, whereby the thicknesses of the membranes are controlled by controlling the number of times a coating solution is applied to the electroactive surface sections. Control of membrane thicknesses in turn permits control of certain membrane properties (e.g., sensitivity, current density, permeability). When in a vertical orientation, the working electrode is dipped into the coating solution at different depths. Because the plurality of electroactive surface sections are spaced apart along the longitudinal axis of the working electrode, by controlling the depth at which the working electrode is dipped into the coating solution, control can be obtained over whether a particular electroactive surface section is coated during a dipping sequence, or how thick the resulting coating is over a particular electroactive surface. For example, in one embodiment, during one dipping sequence, the entire working electrode is dipped five times into the coating solution, so that every electroactive surface section of the working electrode at that time is deposited with a membrane thickness associated with five dips. Subsequently, one or more of the electroactive surface sections (e.g., the one closest to the distal end of the working electrode) is dipped into the coating solution an additional three times, thereby forming in that particular electroactive surface section a membrane with a thickness associated with a total of eight dips. In this particular example, one or more sensor elements are formed with a thickness associated with five dips, while the other sensor element(s) are formed with a thickness associated with eight dips.

The method described above is not limited to the manufacturing of a working electrode comprising two sensor elements, as illustrated in FIG. 1A. The same concept can be applied to working electrodes comprising three, four, five, or more sensor elements. For example, in one embodiment, a first electroactive surface section associated with a first sensor element is dipped into the coating solution for a total of three times to achieve a first thickness, a second electroactive surface section associated with a second sensor element is dipped into the coating solution for a total of five times to achieve a second thickness, and a third electroactive surface section associated with a third sensor element is dipped into the coating solution for a total of seven times to achieve a third thickness.

Figure 6B:
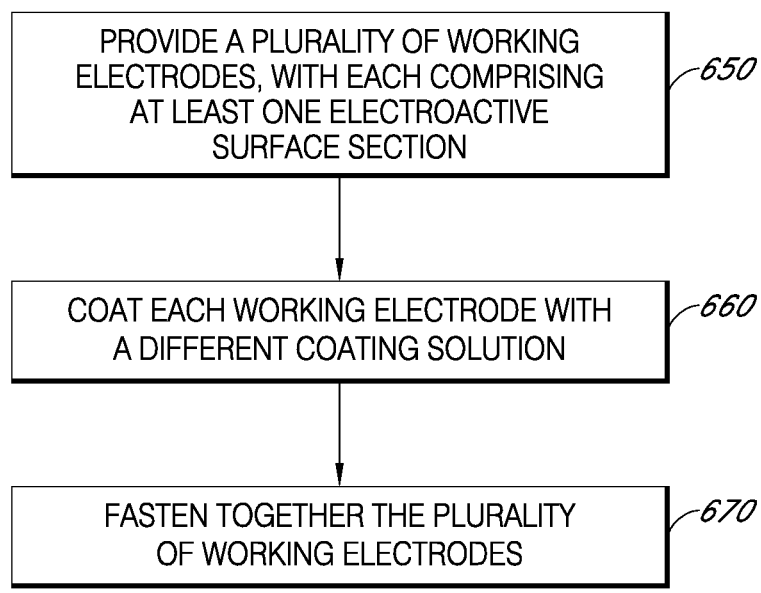
FIG. 6B is a flowchart illustrating another embodiment for manufacturing of a sensor system.

In the embodiments described above, because membrane properties are controlled at least in part by membrane thickness, a single coating solution formulation can be used to form the different membranes. In other embodiments, however, different coating solution formulations are used to form different membranes. For example, as illustrated in FIG. 6B, in one embodiment, in step 650, a plurality of working electrodes are provided, with each working electrode comprising at least one electroactive surface section. Next, in step 660, each working electrode is coated with a different coating solution, resulting in a plurality of working electrodes, with each comprising at least one sensor element with membrane properties different from that of the other sensor element(s) of other working electrode(s). Afterwards, in step 670, the plurality of working electrodes are fastened together to form a sensor system, such as the one illustrated in FIG. 1B, which comprises a plurality of working electrodes, with each comprising at least one sensor element. The method described above is not limited to the manufacturing of a sensor system comprising two working electrodes, with each comprising one sensor element, as illustrated in FIG. 1B. The same concept can be applied to sensor systems comprising three, four, or more working electrodes, with each comprising one, two, three, four, five, or more sensor elements. Additional methods for manufacturing the sensors and membranes described herein are described in Provisional Application No. 61/222,815, filed Jul. 2, 2009 and U.S. patent application Ser. No. 12/829,296, filed Jul. 1, 2010, entitled "ANALYTE SENSORS AND METHOD OF MAKING SAME," each of which is incorporated by reference herein in its entirety.

It is contemplated that in some embodiments, the aforementioned coating methods can be combined. For example, in one embodiment, a sensor system can be formed to comprise three working electrodes, with each working electrode comprising two sensor elements. In a further embodiment, the three working electrodes are each coated with a different coating solution formulation, with each working electrode comprising sensor elements with different membrane thicknesses.

In some embodiments, differences in membrane properties between different sensor elements are achieved by subjecting different sensor elements to different curing processes or conditions. For example, in one embodiment, two electroactive surface sections are coated with one coating solution comprising a polymer system to form a first and a second sensor element. Thereafter, the first sensor element is subjected to high energy UV light for a certain period of time, while the second sensor element is subjected to the same UV light for a different period of time. Thus, in this embodiment, the crosslink densities of the first and second sensor elements are different, thereby resulting in membranes with different sensitivities and current densities. Alternatively, differentiation of membrane properties is achieved by subjecting the sensor elements to other process condition variations, such as differences in radiation (e.g., different wavelengths of light) or differences in temperature, for example. In another example, selective photolithography is used to achieve different sensitivities or current densities, for example, by selectively masking certain membranes associated with certain sensor elements during at least a portion of the photolithographic procedure. In yet another example, a crosslinker is applied to the base polymer (e.g., polyurethane) to create different crosslink densities.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A sensor system for continuous measurement of a glucose concentration in a host, the sensor system comprising:
   a first sensor configured to be implanted in a host and configured to continuously measure a glucose concentration and generate a first signal, wherein the first sensor is associated with a first sensor accuracy during a first time period of a sensor session;
   a second sensor configured to be implanted in the host and configured to continuously measure a glucose concentration and generate a second signal, wherein the second sensor is associated with a second sensor accuracy during the first time period of the sensor session; and
   sensor electronics configured to determine a glucose concentration value based on at least one of the first or the second signal, wherein the sensor electronics are configured to integrate the first signal and the second signal by providing a distribution of weights associated with the first signal and the second signal and by according a first weight to the first signal and according a second weight to the second signal, wherein the distribution of weights among the first and second sensors is a function of time associated with the initiation of the sensor session.

2. The sensor system of claim 1, wherein the first sensor and the second sensor are both configured to generate a signal during a second time period, wherein the first time period corresponds to an initial period of in vivo implantation, wherein the second time period corresponds to a second time period of in vivo implantation, and wherein the second period begins after the initial period of in vivo implantation has begun.

3. The sensor system of claim 2, wherein the first time period and the second time period overlap partially, but not completely.

4. The sensor system of claim 2, wherein the first time period and the second time period do not overlap.

5. The sensor system of claim 2, wherein the first time period begins before less than 3 hours post-implantation, and wherein the second time period begins after more than 3 hours post-implantation.

6. The sensor system of claim 2, wherein the first time period begins before less than 6 hours post-implantation, and wherein the second time period begins after more than 6 hours post-implantation.

7. The sensor system of claim 1, wherein at least one of the first sensor or the second sensor is configured for transcutaneous placement through a skin of a host.

8. The sensor system of claim 1, wherein the sensor system is configured for fluid communication with a vascular system of a host.

9. A method for processing data from a sensor system configured for continuous measurement of a glucose concentration in a host, the method comprising:
   receiving a first signal indicative a glucose concentration in a host from a first sensor;
   receiving a second signal indicative of a glucose concentration in the host from a second sensor; and
   determining during a sensor session, using sensor electronics, a glucose concentration value based on at least one of the first signal or the second signal, wherein determining the glucose concentration value comprises integrating the first signal and the second signal, wherein integrating the first signal and the second signal comprises according a first weight to the first signal and according a second weight to the second signal, and wherein a magnitude of the first weight and a magnitude of the second weight are a function of time associated with an initiation of the sensor session.

10. The method of claim 9, wherein the sensor session comprises a first time period and a second time period.

11. The method of claim 10, wherein the first time period corresponds to an initial period of in vivo implantation, wherein the second time period corresponds to a second time period of in vivo implantation, and wherein the second period begins after the initial period of in vivo implantation has begun.

12. The method of claim 10, wherein the first time period and the second time period overlap partially, but not completely.

13. The method of claim 10, wherein the first time period and the second time period do not overlap.

14. The method of claim 10, wherein the first time period begins before less than 3 hours post-implantation, and wherein the second time period begins after more than 3 hours post-implantation.

15. The method of claim 10, wherein the first time period begins before less than 6 hours post-implantation, and wherein the second time period begins after more than 6 hours post-implantation.

16. The method of claim 9, wherein at least one of the first sensor or the second sensor is configured for transcutaneous placement through a skin of a host.

\* \* \* \* \*

UNITED STATES PATENT AND TRADEMARK OFFICE
CERTIFICATE OF CORRECTION

PATENT NO. : 9,907,497 B2
APPLICATION NO. : 14/057720
DATED : March 6, 2018
INVENTOR(S) : Peter C. Simpson et al.

It is certified that error appears in the above-identified patent and that said Letters Patent is hereby corrected as shown below:

In the Specification

In Column 2 at Line 50, After "membrane" insert --.--.

In Column 4 at Line 8, After "$mm^2$" insert --.--.

In Column 10 at Line 52, Change "andrenostenedione;" to --androstenedione;--.

In Columns 10-11 at Line 67 (Column 10) and at Line 1 (Column 11), Change "diptheria/" to --diphtheria/--.

In Column 11 at Line 7, Change "perioxidase;" to --peroxidase;--.

In Column 11 at Line 13, Change "phenyloin;" to --phenytoin;--.

In Column 11 at Lines 16-17, Change "sissomicin;" to --sisomicin;--.

In Column 11 at Line 21, Change "duodenalisa," to --duodenalis,--.

In Column 11 at Line 28, Change "Trepenoma pallidium," to --Treponema pallidum,--.

In Column 11 at Line 29, Change "stomatis" to --stomatitis--.

In Column 11 at Line 50, Change "(barbituates," to --(barbiturates,--.

Signed and Sealed this
Fifth Day of June, 2018

Andrei Iancu
*Director of the United States Patent and Trademark Office*